(12) United States Patent
Rudolph et al.

(10) Patent No.: US 9,458,142 B2
(45) Date of Patent: Oct. 4, 2016

(54) SUBSTITUTED QUINONES OR ANALOGUES AS COLOURING AGENTS

(71) Applicant: MERCK PATENT GMBH, Darmstadt (DE)

(72) Inventors: Thomas Rudolph, Darmstadt (DE); Rene Peter Scheurich, Gross-Zimmern (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/651,747

(22) PCT Filed: Nov. 14, 2013

(86) PCT No.: PCT/EP2013/003430
§ 371 (c)(1),
(2) Date: Jun. 12, 2015

(87) PCT Pub. No.: WO2014/090364
PCT Pub. Date: Jun. 19, 2014

(65) Prior Publication Data
US 2015/0315177 A1 Nov. 5, 2015

(30) Foreign Application Priority Data

Dec. 13, 2012 (EP) ..................................... 12008325

(51) Int. Cl.
| | |
|---|---|
| *A61Q 5/10* | (2006.01) |
| *C07D 405/12* | (2006.01) |
| *C07D 213/69* | (2006.01) |
| *A61Q 5/06* | (2006.01) |
| *C07D 309/40* | (2006.01) |
| *A61K 8/49* | (2006.01) |
| *C09B 23/14* | (2006.01) |
| *C09B 29/036* | (2006.01) |
| *C09B 29/08* | (2006.01) |
| *C09B 44/10* | (2006.01) |
| *C09B 55/00* | (2006.01) |
| *C09B 57/08* | (2006.01) |
| *C09B 1/26* | (2006.01) |
| *A61Q 5/12* | (2006.01) |
| *A61Q 17/04* | (2006.01) |

(52) U.S. Cl.
CPC ............... *C07D 405/12* (2013.01); *A61K 8/49* (2013.01); *A61K 8/498* (2013.01); *A61K 8/4926* (2013.01); *A61Q 5/06* (2013.01); *A61Q 5/10* (2013.01); *C07D 213/69* (2013.01); *C07D 309/40* (2013.01); *C09B 1/26* (2013.01); *C09B 23/145* (2013.01); *C09B 23/148* (2013.01); *C09B 29/0037* (2013.01); *C09B 29/081* (2013.01); *C09B 29/0811* (2013.01); *C09B 44/103* (2013.01); *C09B 44/105* (2013.01); *C09B 55/003* (2013.01); *C09B 57/08* (2013.01); *A61Q 5/12* (2013.01); *A61Q 17/04* (2013.01)

(58) Field of Classification Search
CPC ........ A61Q 5/10; A61K 8/49; A61K 8/4926; A61K 8/489; C09B 23/145
USPC ............................................................. 8/405
See application file for complete search history.

(56) References Cited

U.S. PATENT DOCUMENTS

| | | | | |
|---|---|---|---|---|
| 4,908,371 | A | * 3/1990 | Moerker | ............. C07D 213/69 514/318 |
| 8,709,104 | B2 | 4/2014 | Rudolph et al. | |
| 2013/0125317 | A1 | 5/2013 | Rudolph et al. | |

FOREIGN PATENT DOCUMENTS

| | | |
|---|---|---|
| WO | 2012028245 A1 | 3/2012 |
| WO | 2012069476 A1 | 5/2012 |

OTHER PUBLICATIONS

STIC Search Report dated Nov. 8, 2015.*
International Search Report dated Feb. 5, 2014 issued in corresponding PCT/EP2013/003430 application (pp. 1-6).
T. Moniz, et al., "Design of a water soluble 1, 8-naphthalimide/3-hydroxy-4-pyridinone conjugate: Investigation of its spectroscopic properties at variable pH and in the prescence of $Fe^{3+}$, $Cu^{2+}$ and $Zn^{2+}$", Dyes and Pigments, vol. 98, No. 2 (May 2013) pp. 201-211.

* cited by examiner

*Primary Examiner* — Eisa Elhilo
(74) *Attorney, Agent, or Firm* — Millen White Zelano & Branigan, P.C.

(57) ABSTRACT

The invention relates to protein-adhesive dyes, to the preparation thereof and to preparations comprising same, and to a method for coloring keratin-containing fibers, in particular for coloring human hair.

10 Claims, No Drawings

SUBSTITUTED QUINONES OR ANALOGUES AS COLOURING AGENTS

DYES

The invention relates to protein-adhesive dyes, the preparation thereof and preparations comprising same, and to a method for dyeing keratin-containing fibres, in particular for dyeing human hair.

At present, a multiplicity of direct dyes is known for the colouring of a matrix, such as, for example, skin, hair, nails or textiles. The dyes here associate onto the matrix and/or form covalent chemical bonds to the matrix. This adhesion and/or bonding of the dye molecules to the matrix can occur in various ways and can give different results with respect to the adhesion character. The dyes are therefore also distinguished by a different adhesion ability or even bonding ability to the respective matrix.

This very bonding ability is often weak in dyes which are common today, meaning that the dye can be washed out rapidly by, for example, sweat or water. Owing to the low ability of the dye to bond to the respective matrix, the yield of the dye in the colouring process is, in addition, low and consequently the intensity of the colouring of matrices may be low. On use of, in particular synthetic, dyes, in particular in the human area of application, low tolerance may additionally be present.

Ascorbic acid derivatives as dyes, in particular of ascorbic acid derivatives which are substituted by colour chromophores in the 6- and/or 5-position, are known, for example, from WO 2012/028245 or WO 2012/069476. During the preparation and storage of these compounds, work is carried out under inert conditions, for example with exclusion of oxygen, since the substances are oxidation-sensitive due to the ascorbic acid basic structure.

Thus, there continues to be a demand for, inter alia, tolerated and in particular skin-tolerated dyes which have good ability of the dye molecules to bond to the respective matrix, enabling the respective matrix to be coloured durably.

Accordingly, the present invention is concerned with the problem of indicating improved or at least alternative dyes for the colouring of matrices which are distinguished, in particular, by an improved colouring behaviour and which have a positive effect on the moisture content of the matrix, which, in the case of application to hair, results in increased hair elasticity.

This problem is solved in accordance with the invention by the subject-matters of the independent claims. Advantageous embodiments are the subject-matter of the dependent claims.

Surprisingly, it has now been established that the compounds of the formula I, as described below, are eminently suitable as protein-adhesive dyes. The term protein-adhesive dye is taken to mean a dye which bonds to a protein-containing matrix owing to at least one adhesion. Preferred matrices here are skin, hair and/or nails, or in other words keratin-containing substrates, in particular keratin-containing fibres. Preferred keratin-containing fibres are hair. Particularly preferred keratin-containing fibres are human hair. The forces for adhesion which effect the cohesion have not been researched fully, and consequently there are various adhesion theories which encompass both mechanical adhesion owing to physical-mechanical forces and specific adhesion owing to chemical and physical forces. It is, for example, possible for the compounds of the formula I, as described below, to interact physically with the matrix molecules, as described above, due to their amphiphilicity or to form a covalent bond to an amino or thiol group of the matrix. The protein-adhesive dyes can accordingly interact physically or form a covalent bond with the matrix. Due to the amphiphilicity, the compounds of the formula I, as described below, also have surface-active properties. The compounds of the formula I, as described below, are preferably skin- or hair-adhesive and/or skin- or hair-bonding dyes. The compounds of the formula I, as described below, are particularly preferably skin-adhesive and/or skin-bonding dyes.

The compounds of the formula I, as described below, are likewise film-forming dyes. Owing to the homogeneous distribution due to uniform surface adhesion and/or bonding, an essential advantage, besides the long-lasting adhesion to the matrix, is that the dye is uniformly distributed on the matrix, in particular uniformly distributed on the keratin-containing fibre, and thus contributes to a uniform colouring result over the entire matrix. In the case of keratin-containing fibres, the uniform colouring result can be achieved from the root to the end of the fibre. It is unimportant for the present invention whether the matrix is a natural or treated matrix, so long as a sufficiently large number of amino or thiol groups remains ensured. Keratin-containing fibres may therefore have been left natural, or also artificially modified, for example in the form of a permanent wave, by blonding or colouring with conventional hair colorants and methods.

Compounds of the formula I according to the invention, as described below, are suitable as antiglycation agents and counter the formation of AGEs (advanced glycation end products).

The invention accordingly relates firstly to the compounds of the formula I,

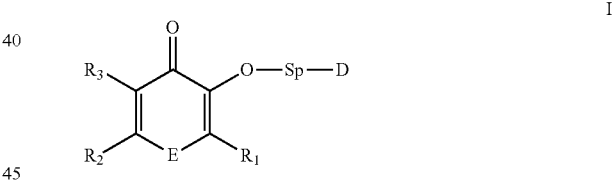

where

E denotes $NR_4$ or O,

Sp denotes a bond, alk, —C(O)— or —(CO)-alk,

D denotes a colour chromophore, $R_1$, $R_2$ or $R_3$ each, independently of one another, denote —H, -A, —OA-, —$(CH_2)_p$—OH, —C(O)OA, COOH or COOX, p denotes an integer from 1 to 4, X is the counterion to the [COO$^-$] group, $R_4$ denotes A, alk denotes a linear or branched or cyclic alkylene group having 1 to 18 C atoms and A denotes a linear or branched alkyl group having 1 to 20 C atoms and/or salts, tautomers, stereoisomers and/or solvates thereof, including mixtures thereof in all ratios.

The invention accordingly furthermore relates to the use of compounds of the formula I,

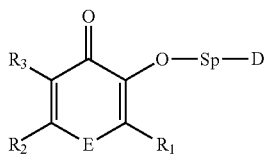

where

E denotes $NR_4$ or O,

Sp denotes a bond, alk, —C(O)— or —(CO)-alk,

D denotes a colour chromophore, $R_1$, $R_2$ or $R_3$ each, independently of one another, denote —H, -A, —OA-, —$(CH_2)_p$—OH, —C(O)OA, COOH or COOX, p denotes an integer from 1 to 4, X is the counterion to the [COO⁻] group, $R_4$ denotes A, alk denotes a linear or branched or cyclic alkylene group having 1 to 18 C atoms and A denotes a linear or branched alkyl group having 1 to 20 C atoms and/or salts, tautomers, stereoisomers and/or solvates thereof, including mixtures thereof in all ratios as protein-adhesive dyes.

For the purposes of the invention, the compounds of the formula I, are defined in such a way that they are also taken to mean pharmaceutically or cosmetically usable derivatives, salts, hydrates, solvates, precursors of the compounds, tautomers and optically active forms (such as, for example, stereoisomers, diastereomers, enantiomers, racemates). Solvates of the compounds are taken to mean adductions of inert solvent molecules onto the compounds which form owing to their mutual attractive force. Solvates are, for example, mono- or dihydrates or alcoholates. Pharmaceutically or cosmetically usable derivatives are taken to mean, for example, the salts of the compounds according to the invention. The compounds of the formula I can form cis/trans isomers or tautomers. The formula I encompasses all these forms.

A base of the formula I can be converted into the associated acid-addition salt using an acid, for example by reaction of equivalent amounts of the base and the acid in an inert solvent, such as ethanol, and subsequent evaporation. Suitable acids for this reaction are, in particular, those which give physiologically acceptable salts. On the other hand, acids of the formula I can be converted into the corresponding metal salts, in particular alkali-metal or alkaline-earth metal salts, or into the corresponding ammonium salts using bases (for example sodium hydroxide or carbonate or potassium hydroxide or carbonate).

The abbreviation "A" stands for alkyl having 1 to 20 C atoms, i.e. in other words for a linear or branched alkyl group having 1 to 20 C atoms, for example methyl, ethyl, isopropyl, propyl, butyl, sec-butyl or tert-butyl, furthermore pentyl, 1-, 2- or 3-methylbutyl, 1,1-, 1,2- or 2,2-dimethylpropyl, 1-ethylpropyl, n-hexyl, n-heptyl, n-octyl, furthermore nonyl, decyl, undecyl, dodecyl, tridecyl, tetradecyl, pentadecyl, hexadecyl, heptadecyl, octadecyl, nonadecyl and eicosyl. From the straight-chain or branched alkyl group having 1 to 20 C atoms, the straight-chain or branched alkyl group having 1 to 8 C atoms, i.e. methyl, ethyl, isopropyl, propyl, butyl, sec-butyl or tert-butyl, furthermore pentyl, 1-, 2- or 3-methylbutyl, 1,1-, 1,2- or 2,2-dimethylpropyl, 1-ethylpropyl, n-hexyl, n-heptyl, n-octyl, is preferably selected. From the straight-chain or branched alkyl group having 1 to 20 C atoms, the straight-chain or branched alkyl group having 1 to 4 C atoms, i.e. methyl, ethyl, isopropyl, propyl, butyl, sec-butyl or tert-butyl, is particularly preferably selected.

The abbreviation "alk" stands for a linear or branched or cyclic alkylene group having 1 to 18 C atoms is derived from the alkyl groups having 1 to 18 C atoms described above. alk preferably stands for methylene, ethylene, propylene or butylene.

The abbreviation —OA stands for O-alkyl having 1 to 20 C atoms, analogously for alkoxy having 1 to 20 C atoms, where A is used as defined above.

Correspondingly, the abbreviation —NHA stands for alkylamino and —$NA_2$ stands for dialkylamino.

X describes the counterion for the cations $[NHA_2]^+$ and $[NA_3]^+$, where A has one of the meanings indicated above, preferably Cl⁻, Br⁻, I⁻ or $[SO_4]^{2-}$, or the counterion of the anion [COO]⁻ or $[SO_3]^-$, preferably an ammonium ion or an alkali metal or alkaline-earth metal cation, such as Na⁺, K⁺, $Mg^{2+}$ or $Ca^{2+}$.

In an embodiment, preference is given to compounds of the formula I in which the substituent $R_1$ denotes A and A has one of the meanings indicated above or meanings indicated as preferred. $R_1$ is particularly preferably methyl or ethyl. $R_1$ is very particularly preferably methyl.

In an embodiment, preference is given to compounds of the formula I in which the substituent $R_2$ denotes H, —$(CH_2)_p$—OH, —C(O)OA, COOH or COOX, where A, X and p have a meaning indicated above or preferably indicated. The substituent $R_2$ is particularly preferably H, hydroxymethyl or —C(O)O-ethyl or —C(O)O-methyl. The substituent $R_2$ is very particularly preferably H.

In an embodiment, preference is given to compounds of the formula I in which the substituent $R_3$ denotes H.

In a preferred embodiment, preference is given to compounds of the formula I in which the substituents $R_2$ and $R_3$ denote H.

In an embodiment, preference is given to compounds of the formula I in which the substituent $R_4$ denotes A and A has one of the meanings indicated as preferred. $R_4$ is particularly preferably methyl or ethyl. $R_4$ is very particularly preferably methyl.

In a preferred embodiment, preference is given to compounds of the formula I in which the variable E denotes O or $NR_4$ and the substituents $R_4$, $R_3$, $R_2$ and $R_1$ have one of the preferred meanings indicated above or indicated below or have meanings particularly preferably indicated.

Accordingly, the compounds of the formulae I-a, I-b, I-c and I-d are particularly preferred:

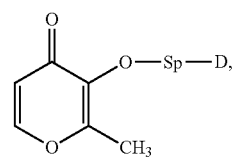

I-a

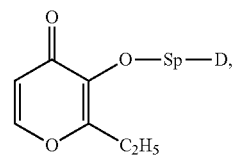

I-b

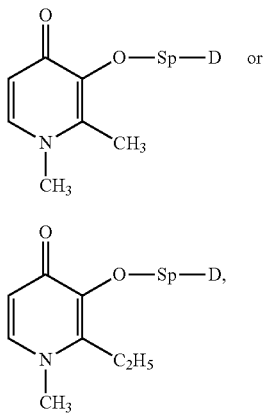

where Sp and D have one of the meanings indicated above or below or have one of the preferred meanings indicated below.

In an embodiment, preference is given to compounds of the formula I in which the variable E denotes O.

In an embodiment, preference is given to compounds of the formula I in which the variable E denotes N—$R_4$ and $R_4$ denotes A, where A has one of the meanings indicated or preferably indicated above. The variable E preferably denotes N-methyl.

In a preferred embodiment, preference is given to compounds of the formula I in which the variable E denotes O and the substituents $R_3$, $R_2$, $R_1$, Sp and D have one of the preferred meanings or particularly preferred meanings indicated above or indicated below. In this embodiment, the compounds of the formula I-a or I-b are particularly preferred. In this embodiment, the compounds of the formula I-a are very particularly preferred.

In a preferred embodiment, preference is given to compounds of the formula I in which the variable E denotes $NR_4$ and the substituents $R_4$, $R_3$, $R_2$, $R_1$, Sp and D have one of the preferred meanings or particularly preferred meanings indicated above or indicated below. In this embodiment, the compounds of the formula I-c or I-d are particularly preferred. In this embodiment, the compounds of the formula I-c are very particularly preferred.

In a preferred embodiment, preference is given to compounds of the formula I, I-a, I-b, I-c or I-d in which the variable Sp denotes —C(O)—.

The nature of the colour chromophore D is not restricted for the purposes of the present invention. The advantageous properties of the compounds of the formula I, I-a, I-b, I-c or I-d, as described above, are achieved by the structural unit of the formula I-1,

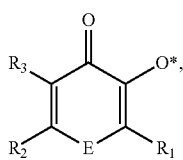

I-1 where $R_1$, $R_2$, $R_3$ and E have a meaning given above for the compounds of the formula I, I-a, I-b, I-c and I-d or have a meaning indicated as preferred.

The colour chromophore D is derived from a dye which is able to colour the matrix, as described above, and/or which is itself coloured, i.e. is capable of absorbing radiation in the range between 250 nm and 800 nm. The colour chromophore D is preferably derived from a dye which absorbs radiation in the visible region between 400 and 700 nm.

The colour chromophore D may also have been derived from a fluorescent dye, so that a compound of the formula I, I-a, I-b, I-c or I-d containing this fluorescent colour chromophore also becomes visible on a matrix which already appears dark.

A fluorescent colour chromophore D is derived from a fluorescent dye which is able to colour the matrix, as described above, and/or which is itself coloured, i.e. is capable of absorbing radiation in the range between 250 nm and 800 nm and which is able to re-emit at least part of the absorbed light. The fluorescent colour chromophore D is preferably derived from a fluorescent dye which absorbs radiation in the visible region between 400 and 800 nm and emits radiation between 410 and 810 nm. The fluorescent colour chromophore D is particularly preferably derived from a fluorescent dye which absorbs radiation in the visible region between 420 and 550 nm and emits radiation between 470 and 600 nm.

The colour chromophore D can accordingly be derived from the following dyes: acridine dyes, acridone dyes, anthrapyrimidine dyes, anthraquinone dyes, azine dyes, (poly)-azo dyes, hydrazono dyes, hydrazone dyes, preferably arylhydrazone dyes, azomethine dyes, benzanthrone dyes, benzimidazole dyes, benzimidazolone dyes, benzindole dyes, benzoxazole dyes, benzopyran dyes, benzothiazole dyes, benzoquinone dyes, bisazine dyes, bisisoindoline dyes, carboxanilide dyes, coumarine dyes, cyanine dyes, for example merocyanine dyes, azacarbocyanine dyes, diazacarbocyanine dyes, diazahemicyanine dyes, hemicyanine dyes or tetraazacarbocyanine dyes, diazine dyes, diketopyrrolopyrrole dyes, dioxazine dyes, diphenylamine dyes, diphenylmethane dyes, dithiazine dyes, flavonoids for example flavanthrones and flavones, fluorindine dyes, formazane dyes, indamine dyes, indanthrone dyes, indigoids and pseudoindigoids, indophenol dyes, indoaniline dyes, isoindoline dyes, isoindolinone dyes, isoviolanthrone dyes, lactone dyes, (poly)methine dyes, for example dimethine dyes of the stilbene or styrene type, naphthalimide dyes, naphthanilide dyes, naphtholactam dyes, naphthoquinone dyes, dyes containing at least one $NO_2$ group, oxadiazole dyes, oxazine dyes, perilone dyes, perinone dyes, perylene dyes, phenazine dyes, phenoxazine dyes, phenothiazine dyes, phthalocyanine dyes, polyenes or carotinoids, porphyrin dyes, pyranthrone dyes, pyrazolanthrone dyes, pyrazolone dyes, pyrimidinoanthrone dyes, pyronine dyes, quinacridone dyes, quinoline dyes, quinophathalone dyes, swuarane dyes, tetrazole dyes, thiazine dyes, thioindigo dyes, thiopyronine dyes, triarylmethane dyes or xanthene dyes.

In accordance with the invention, preference is given to compounds of the formula I, I-a, I-b, I-c or I-d, as described above or described as preferred, if the colour chromophore D conforms to one of the formulae II, III, IV, V, VI, VII, VIII, IX, X, XI or XII, where the marking * in the formulae described below denotes the linking site to the spacer Sp, preferably denotes the linking site to the spacer —C(O)—:

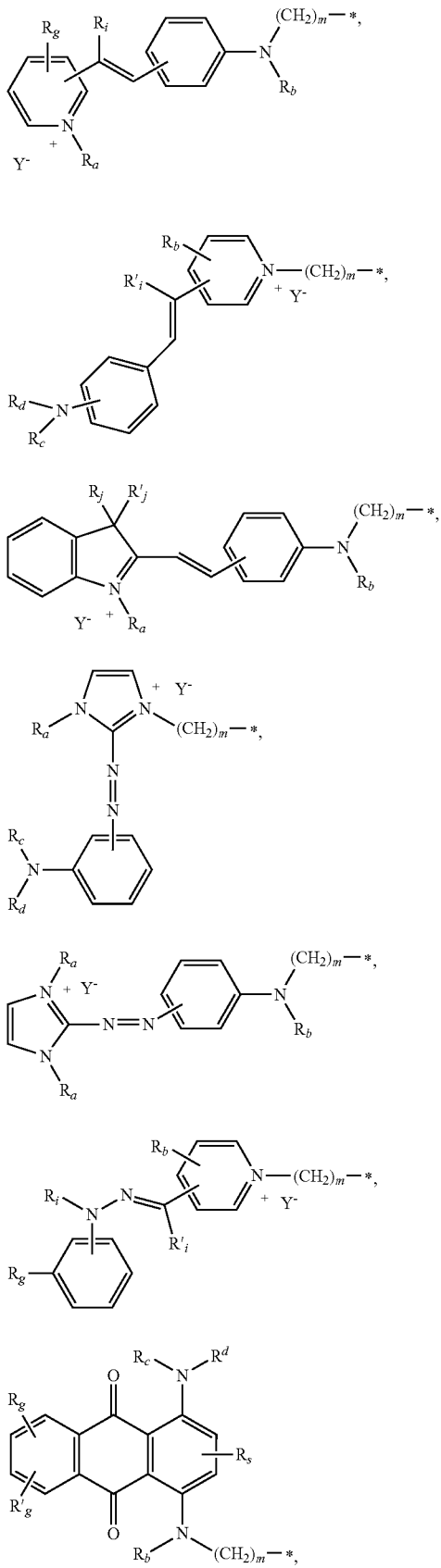

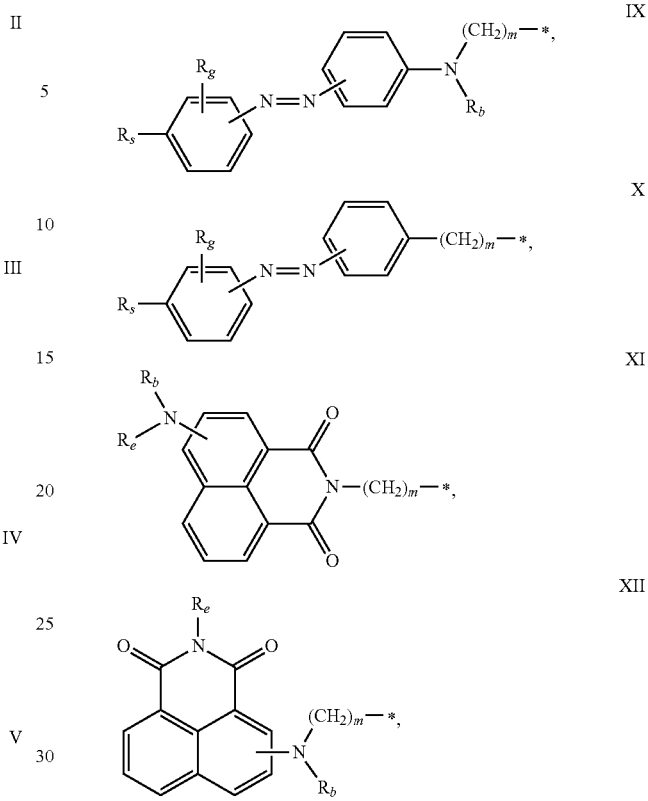

where
$R_a$, $R_j$ and $R'_j$ each, independently of one another, denote A, $R_b$ denotes H or A, $R_g$ and $R'_g$ each, independently of one another, denote H, Hal, $NA_2$, CN, COOH, OH, $CF_3$, OA, OC(O)A, C(O)OA, NHC(O)A, $NHSO_2A$, $SO_2NA_2$, $R_s$ denotes H, A, $NA_2$, OA or $SO_3Y$, $R_i$ and $R'_i$ each, independently of one another, denote H or A, $R_c$ and $R_d$ each, independently of one another, denote H or A, where A may be substituted by at least one OH group, $R_e$ denotes an alkyl group having 1 to 6 C atoms which is substituted by at least one group $NA_2$ or $NA_3Y$, Y is an anion of an organic or inorganic acid or a cation, A denotes a linear or branched alkyl group having 1 to 20 C atoms, Hal denotes F, Cl, Br or I and m denotes 0, 1, 2, 3, 4 or 5.

The abbreviation "A" has been described above and the comments regarding "A", "OA", "NHA", "$NA_2$" also apply correspondingly to the formulae II to XII.

Hal denotes halogen or in other words F, Cl, Br or I. Hal is preferably Br or I.

The anion Y corresponds to an organic or inorganic acid which is tolerated pharmacologically or from a cosmetic point of view or to a cation. Examples of the anion Y are, as described above, $F^-$, $Cl^-$, $Br^-$, $I^-$ or $[SO_4]^{2-}$. Examples of Y as cation include $Na^+$, $K^+$, $Mg^{++}$, $Ca^{++}$, $NH_4^+$ and quaternary ammonium salts.

The variable m denotes 0, 1, 2, 3, 4 or 5. Preferred meanings are indicated specifically in the case of the formulae II to XII.

Preferred embodiments of the colour chromophore D which is described by the formulae II, III, IV, V, VI, VII, VIII, IX, X, XI and XII are listed below. Each preferred or particularly preferred embodiment of one of the said formulae II to XII can be combined with one or more of the said preferred or particularly preferred embodiments of the other formulae II to XII in order preferably to describe the selection of the colour chromophore D in the compounds of the formula I, I-a, I-b, I-c or I-d.

In an embodiment of the substituents of the formula II, $R_i$ is H. In a further embodiment of the substituents of the formula II, $R_i$ is H and $R_a$ and $R_b$ are each, independently of one another, A, where A has one of the meanings indicated above or meanings indicated as preferred. In a further embodiment of the substituents of the formula II, $R_i$ is H and $R_a$ and $R_b$ are each, independently of one another, A, where A has one of the meanings indicated above or meanings indicated as preferred and $R_g$ is H. In formula II, m is preferably 1. In formula II, Y is preferably chloride, bromide, an alkylsulfate or alkyl ether sulfate, such as, for example, laurylsulfate or lauryl ether sulfate.

In an embodiment of the substituents of the formula III, $R'_i$ is H. In a further embodiment of the substituents of the formula III, $R'_i$ is H and $R_c$ and $R_d$ are each, independently of one another, A, where A may be substituted by at least one OH group. A here has one of the meanings indicated above or meanings indicated as preferred, where the said alkyl groups having 1 to 20 C atoms may additionally be substituted by at least one OH group. In a further embodiment of the substituents of the formula III, $R'_i$ is H and $R_c$ and $R_d$ are each identical, where A is preferably selected from a linear or branched alkyl group having 1 to 8 C atoms or a linear or branched alkyl group having 1 to 8 C atoms which is substituted by an OH group. In formula III, $R_c$ and $R_d$ are particularly preferably selected from methyl or 2-hydroxyethyl. In formula III, $R_b$ is preferably H. In formula III, m is preferably 2 or 3, particularly preferably 2. In formula III, Y is preferably chloride, bromide, an alkylsulfate or alkyl ether sulfate, such as, for example, laurylsulfate or lauryl ether sulfate.

In a preferred embodiment of the substituents of the formula III, $R'_i$ is H, $R_c$ and $R_d$ are identical and are selected from a linear or branched alkyl group having 1 to 8 C atoms or a linear or branched alklyl group having 1 to 8 C atoms which is substituted by an OH group, $R_g$ is H and m is 3 or 4.

In an embodiment of the substituents of the formula IV, $R_j$ and $R'_j$ are methyl. In a further embodiment of the substituents of the formula IV, $R_j$ and $R'_j$ are methyl and $R_a$ and $R_b$ are each, independently of one another, A, where A has one of the meanings indicated above or meanings indicated as preferred. In formula IV, m is preferably 1. In formula IV, Y is preferably chloride, bromide, an alkylsulfate or alkyl ether sulfate, such as, for example, laurylsulfate or lauryl ether sulfate.

In an embodiment of the substituents of the formula V, $R_a$ is methyl. In a further embodiment of the substituents of the formula V, $R_a$ is methyl and $R_c$ and $R_d$ are each identical, where A is preferably selected from a linear or branched alkyl group having 1 to 8 C atoms or a linear or branched alkyl group having 1 to 8 C atoms which is substituted by an OH group. In formula V, $R_c$ and $R_d$ are particularly preferably selected from methyl or 2-hydroxyethyl. In formula V, m is preferably 3. In formula V, Y is preferably chloride, bromide, an alkylsulfate or alkyl ether sulfate, such as, for example, laurylsulfate or lauryl ether sulfate.

In an embodiment of the substituents of the formula VI, $R_b$ is methyl. In a further embodiment of the substituents of the formula VI, $R_b$ is methyl and $R_a$ is in each case identical, where A has one of the meanings indicated above or meanings indicated as preferred. In formula VI, m is preferably 1. In formula VI, Y is preferably chloride, bromide, an alkylsulfate or alkyl ether sulfate, such as, for example, laurylsulfate or lauryl ether sulfate.

In an embodiment of the substituents of the formula VII, $R_i$ and $R'_i$ are H. In a further embodiment of the substituents of the formula VII, $R_i$ and $R'_i$ are H and $R_b$ is H. In formula VII, $R_g$ is preferably H. In formula VII, m is preferably 3 or 4, particularly preferably 3. In formula VII, Y is preferably chloride, bromide, an alkylsulfate or alkyl ether sulfate, such as, for example, laurylsulfate or lauryl ether sulfate.

In an embodiment of the substituents of the formula VIII, $R_b$ is H or methyl. In a further embodiment of the substituents of the formula VIII, $R_b$ is H or methyl and $R_g$ and $R'_g$ are H. In formula VIII, $R_c$ and $R_d$ are preferably both H or both methyl. In formula VIII, m is preferably 3 or 4, particularly preferably 3. In formula VIII, Y is preferably sodium, potassium, ammonium or a quaternary ammonium compound.

In an embodiment of the substituents of the formula IX, $R_b$ is methyl. In a further embodiment of the substituents of the formula IX, $R_b$ is methyl and $R_g$ is H. In formula IX, m is preferably 1. In formula IX, Y is sodium, potassium, ammonium or a quaternary ammonium compound.

In an embodiment of the substituents of the formula X, m is 0. In a further embodiment of the substituents of the formula X, m is 0 and $R_g$ is H. In formula X, $R_s$ is preferably H or $NA_2$, where A has a meaning indicated above or a meaning indicated as preferred.

In an embodiment of the substituents of the formula XI, $R_b$ is H. In a further embodiment of the substituents of the formula XI, $R_b$ is H and $R_e$ is an alkyl group having 3 C atoms which is substituted by at least one group $NA_2$ or $NA_3Y$, where A has a meaning indicated above or a meaning indicated as preferred. In formula XI, m is preferably 5. In formula XI, Y is preferably chloride, bromide, an alkylsulfate or alkyl ether sulfate, such as, for example, laurylsulfate or lauryl ether sulfate.

In an embodiment of the substituents of the formula XII, $R_b$ is methyl. In a further embodiment of the substituents of the formula XII, $R_b$ is methyl and $R_e$ is an alkyl group having 4 C atoms which is substituted by at least one group $NA_2$ or $NA_3Y$, where A has a meaning indicated above or a meaning indicated as preferred. In formula XII, m is preferably 1. In formula XII, m is preferably 5. In formula XI, Y is preferably chloride, bromide, an alkylsulfate or alkyl ether sulfate, such as, for example, laurylsulfate or lauryl ether sulfate.

Particularly preferred embodiments of the radical D are to be seen in the following moieties:

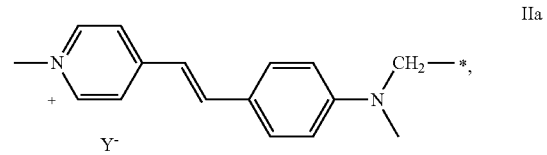

IIa

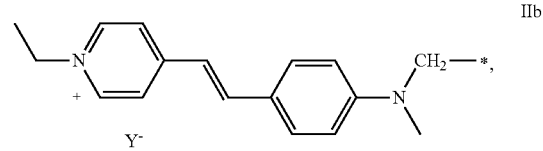

IIb

IIc IId IIIa IIIb IIIc IIId IIIe IIIf IIIg IIIh IVa IVb IVc

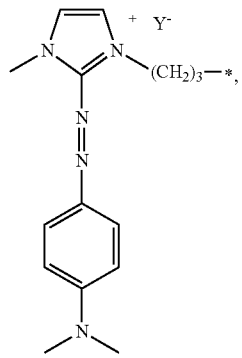
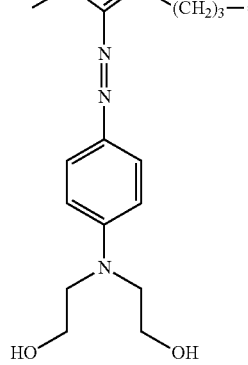
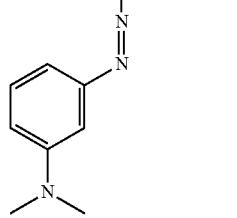
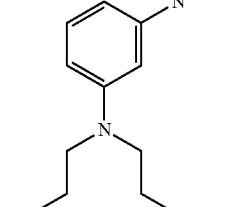
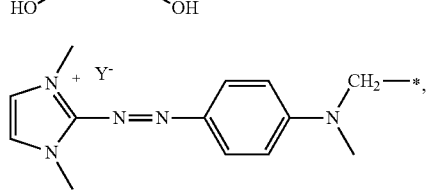
Va
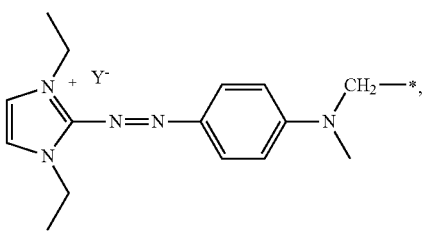
Vb
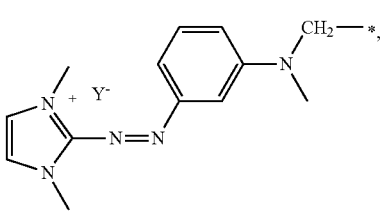
Vc
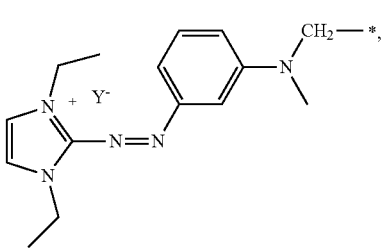
Vd
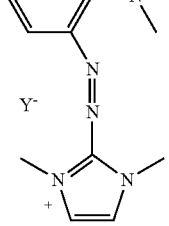
VIa
VIc
VId
VIe
VIIa
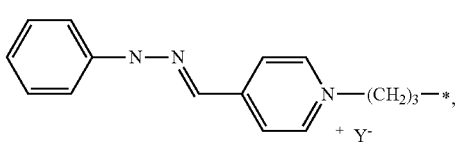
VIIb
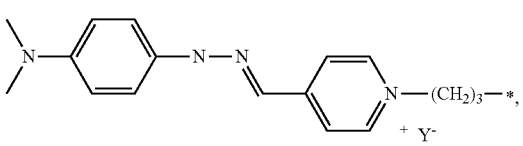
VIIc
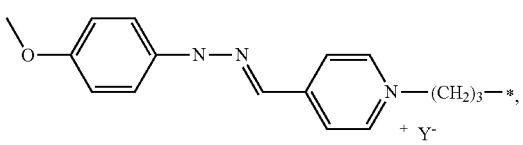
VIId
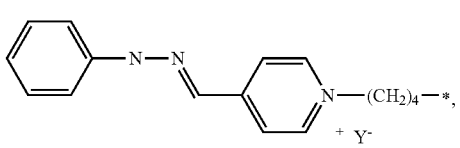

-continued

VIIe, VIIf, VIIg, VIIIa, VIIIb, VIIIc, VIIId, IXa, IXb, IXc, IXd, Xa, Xb, Xc, Xd, Xe, XIa, XIb, XIc

-continued

XId
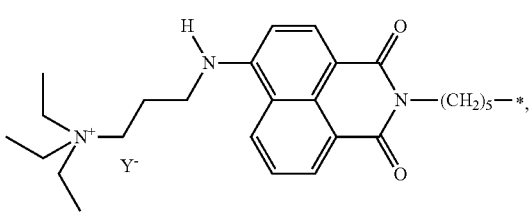

XIIa
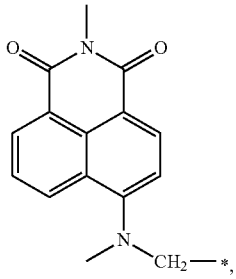

XIIb
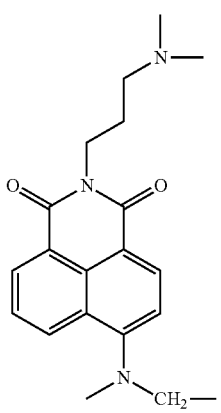

XIIc
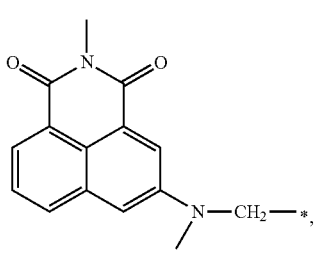

XIId
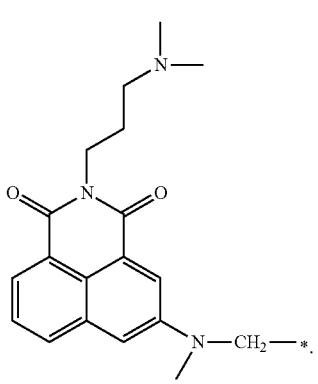

Preferred colour chromophores D conform to the formulae III, X or XI, where the radicals R'$_l$, R$_b$, R$_c$, R$_d$, m, Y, R$_s$, R$_g$ and R$_e$ have one of the meanings indicated above or preferably indicated or conform to the corresponding part-formulae IIIa-IIIg, Xa-Xe or XIa-XId.

D very particularly preferably conforms to the formula X, where R$_g$ and R$_s$ have a meaning indicated above or preferred meaning, in particular conform to the part-formulae Xa to Xe.

The preparation of the compounds of the formula I, I-a, I-b, I-c, I-d, as described above, can be carried out here by methods known per se to the person skilled in the art from the literature. The reaction conditions for esterifications or etherifications are standard prior art and the selection of the suitable reaction conditions belongs to the standard expert knowledge of the person skilled in the art of synthesis.

The invention likewise relates to a process for the preparation of compounds of the formula I, I-a, I-b, I-c, I-d, as described above or described as preferred, characterised in that a compound of the formula XIII XIII
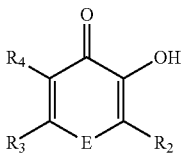

in which R$_2$, R$_3$, R$_4$ and E have a meaning given above, is reacted with a compound of the formula XIV D-Sp-M     XIV, in which D and Sp have a meaning given above, and M denotes alkali-metal or alkaline-earth metal cation, halogen, OH or H or a compound of the formula XIII, in which R$_2$, R$_3$, R$_4$ and E have meaning given above, is reacted with an active ester of the compound of the formula XIV, derived from the free acid of the formula XIV, in which M denotes OH and Sp denotes —C(O)— and D has a meaning given above.

Some of the compounds of the formula XIII are commercially available, for example 3-hydroxy-2-methyl-4-pyranone, or can be prepared by known literature methods, for example based on R. Suzuki et al, Heterocyles, 1977, 6(9-10), 1575-80 or A. Fassihi et al, European Journal of Medicinal Chemistry, 2009, 44(5), 2145-2157).

Some of the compounds of the formula XIV are commercially available, or can be synthesised by methods which are described, for example, in the standard works, such as Houben-Weyl, Methoden der organischen Chemie [Methods of Organic Chemistry], Georg-Thieme-Verlag, Stuttgart, to be precise under reaction conditions which are known and suitable for the said reactions. Use can also be made here of variants known per se which are not mentioned here in greater detail. Commercially available dyes are listed, for example, in the Colour Index International.

The ether formation by reaction of compounds of the formula XIV in which Sp denotes a single bond or alk and in which M=Hal with a compound of the formula XIII, as described above, preferably takes place in the presence of triphenylphosphine and diisopropyl azodicarboxylate, in an inert solvent, for example a halogenated hydrocarbon, such as dichloromethane, an ether, such as tetrahydrofuran or dioxane, an amide, such as DMF or dimethylacetamide, a nitrile, such as acetonitrile, in dimethyl sulfoxide or in the presence of these solvents, at temperatures between about −10 and 40, preferably between 0 and 30°. The reaction time is between a few minutes and several days, depending on the conditions used.

If an acid halide or an active ester of the free acid of the formula XIV are employed for the synthesis of the compounds of the formula I as described above, a classical nucleophilic substitution takes place. The reaction conditions of a nucleophilic substitution are adequately known to the person skilled in the art of synthesis.

Preferred acid halides of the formula XIV are acid chlorides.

If a compound of the formula XIII, as described above, for example 3-hydroxy-2-methyl-4-pyranone, is reacted with a compound of formula XIV in which Sp is —C(O)— and M=H and D denotes a colour chromophore, as described above, the coupling reaction is preferably carried out in the presence of a dehydrating agent, for example a carbodiimide, such as dicyclohexylcarbodiimide (DCC), N-(3-dimethylaminopropyl)-N'-ethylcarbodiimide hydrochloride (EDC) or diisopropylcarbodiimide (DIC), furthermore, for example, propanephosphonic anhydride (cf. Angew. Chem. 1980, 92, 129), diphenylphosphoryl azide or 2-ethoxy-N-ethoxycarbonyl-1,2-dihydroquinoline, in an inert solvent, for example a halogenated hydrocarbon, such as dichloromethane, an ether, such as tetrahydrofuran or dioxane, an amide, such as DMF or dimethylacetamide, a nitrile, such as acetonitrile, in dimethyl sulfoxide or in the presence of these solvents, at temperatures between about −10 and 40, preferably between 0 and 30°. Depending on the conditions used, the reaction time is between a few minutes and several days.

Instead of compounds of the formula XIV, as defined above, it is also possible to employ derivatives of the formula XIV, preferably a pre-activated carboxylic acid or a carboxylic acid halide, a symmetrical or mixed anhydride or an active ester. Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example by addition of HOBt (1-hydroxybenzotriazole) or N-hydroxysuccinimide.

The reaction is generally carried out in an inert solvent, in the case of the use of an acid halide in the presence of an acid-binding agent, preferably an organic base, such as triethylamine, dimethylaniline, pyridine, dimethylaminopyridine or quinoline.

The addition of an alkali-metal or alkaline-earth metal hydroxide, carbonate or bicarbonate or of another salt of a weak acid of the alkali or alkaline-earth metals, preferably of potassium, sodium, calcium or caesium, may also be favourable.

The compounds of the formula I, I-a, I-b, I-c or I-d according to the invention, as described above or as preferably described, are oxidation-stable and exhibit a reduced yellow colouration or no yellow colouration on storage.

Compounds of the formula I according to the invention, as described above, are likewise suitable as anti-glycation agents and counter the formation of AGEs (advanced glycation end products).

Compounds according to the invention are suitable as contrast reduction agents, i.e. they may be able to lighten dark skin areas or darken light skin areas.

A further idea of the invention is a method for colouring a matrix, in particular a protein-containing matrix, in which the matrix is coloured directly in one colouring step by the action of a dispersion and/or solution and/or emulsion of a compound of the formula I, I-a, I-b, I-c or I-d, as described above, on the matrix.

In a pretreatment step, the matrix can be pretreated here by means of a pretreatment agent in order to influence and in particular to improve the colouring behaviour thereof. A pretreatment agent of this type may be basic, acidic or neutral, have an oxidative action, for example due to the presence of an oxidant, such as hydrogen peroxide, and optionally contain water. The pretreatment step is usually carried out before the colouring step.

The invention furthermore relates to preparations which comprise at least one compound of the formula I, I-a, I-b, I-c or I-d, as described above.

The preparation here is usually a preparations which can be applied topically, for example cosmetic or dermatological formulations or medical devices. In this case, the preparations comprise a cosmetically or dermatologically suitable carrier and, depending on the desired property profile, optionally further suitable ingredients. In the case of pharmaceutical preparations, the preparations in this case comprise a pharmaceutically tolerated carrier and optionally further pharmaceutical active compounds. In the case of medical devices, the preparations comprise a carrier which is suitable for the medical device.

Can be applied topically here means that the preparation is applied externally and locally, i.e. that the preparation must be suitable for, for example, application to the skin.

The topical preparations are preferably employed as cosmetic or dermatological preparation, particularly preferably as cosmetic preparation.

The term preparation is also synonymously taken to mean composition or formulation.

The preparations may include or comprise, essentially consist of or consist of the said requisite or optional constituents. All compounds or components which can be used in the preparations are either known and commercially available or can be synthesised by known processes.

In preferred embodiments, the at least one compound of the formula I, I-a, I-b, I-c or I-d having the substituents defined or indicated as preferred is typically employed in the preparations according to the invention in amounts of 0.05 to 10% by weight, preferably in amounts of 0.1% by weight to 5% by weight and particularly preferably in amounts of 0.5 to 2% by weight.

The invention furthermore relates to a process for the preparation of a preparation of this type, as described above, in which at least one compound of the formula I, I-a, I-b, I-c or I-d, as described above, is mixed, in particular is dispersed and/or emulsified and/or dissolved, with at least one vehicle which is suitable for cosmetic, pharmaceutical, dermatological preparations, medical devices or household products and optionally assistants and/or fillers. Suitable vehicles as well as active substances or assistants are described in detail in the following part.

The preparation is preferably designed as multicomponent system, in which at least one compound of the formula I, as described above, as development component, at least one coupling component, optionally a pretreatment agent, optionally a further development component and/or at least one oxidant are distributed over at least two preparation components. A first preparation component preferably has at least one compound of the formula I and at least one coupling component and at least one vehicle which is suitable for cosmetic, pharmaceutical, dermatological preparations or household products and optionally at least one non-oxidative pretreatment agent, while a second coupling component has at least one oxidant, in particular hydrogen peroxide.

Furthermore, in order, for example, to be able to carry out further colour adaptations, the compounds of the formula I, I-a, I-b, I-c or I-d can be combined with previously known oxidation dye components.

Suitable oxidation dye components of the developer type are p-phenylenediamine and derivatives thereof. Suitable p-phenylenediamines are selected from one or more compounds from the group formed by p-phenylenediamine, p-tolylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(2-hydroxyethyl)-p-phenylenediamine, 4-N,N-bis-(2-hydroxyethyl)amino-2-methylaniline, 4-N,N-bis-(2-hydroxyethyl)-amino-2-chloroaniline, 2-(2-hydroxyethyl)-p-phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N-2-hydroxyethyl-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazol-1-yl)propyl]amine, 5,8-diaminobenzo-1,4-dioxane and physiologically tolerated salts thereof. Further suitable p-phenylenediamine derivatives are selected from at least one compound from the group p-phenylenediamine, p-tolylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, 2-methoxymethyl-p-phenylenediamine and the physiologically tolerated salts of these compounds.

Further suitable developer components which can be employed are compounds which contain at least two aromatic rings which are substituted by amino and/or hydroxyl groups. Further suitable developer components are selected, in particular, from at least one compound from the group formed by N,N'-bis-(2-hydroxyethyl)-N,N'-bis-(4'-aminophenyl)-1,3-diaminopropan-2-ol, N,N'-bis-(2-hydroxyethyl)-N,N'-bis-(4'-aminophenyl)ethylenediamine, N,N'-bis-(4'-aminophenyl)tetramethylenediamine, N,N'-bis-(2-hydroxyethyl)-N,N'-bis-(4'-aminophenyl)-tetramethylenediamine, N,N'-bis-(4-(methylamino)phenyl)tetramethylenediamine, N,N'-diethyl-N,N'-bis-(4'-amino-3'-methylphenyl)ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl)piperazine, N-(4'-aminophenyl)-p-phenylenediamine and 1,10-bis-(2',5'-diaminophenyl)-1,4,7,10-tetraoxadecane and physiologically tolerated salts thereof. Further suitable bicyclic developer components are selected from N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxyl)propan-2-ol, N,N'-bis-(4-aminophenyl)-1,4-diazacycloheptane, 1,10-bis-(2,5-diaminophenyl)-1,4,7,10-tetraoxadecane or one of the physiologically tolerated salts of these compounds.

It may furthermore be possible to employ a p-aminophenol derivative or one of its physiologically tolerated salts as developer component. Preferred p-aminophenols are p-aminophenol, N-methyl-p-aminophenol, 4-amino-3-methylphenol, 4-amino-3-fluorophenol, 2-hydroxymethyl-amino-4-aminophenol, 4-amino-3-hydroxymethylphenol, 4-amino-2-(2-hydroxyethoxyl)phenol, 4-amino-2-methylphenol, 4-amino-2-hydroxymethylphenol, 4-amino-2-methoxymethylphenol, 4-amino-2-aminomethylphenol, 4-amino-2-(2-hydroxyethylaminomethyl)phenol, 4-amino-2-(1,2-dihydroxyethyl)phenol, 4-amino-2-fluorophenol, 4-amino-2-chlorophenol, 4-amino-2,6-dichlorophenol, 4-amino-2-(diethylaminomethyl)phenol and physiologically tolerated salts thereof. Particularly preferred compounds are p-aminophenol, 4-amino-3-methylphenol, 4-amino-2-aminomethylphenol, 4-amino-2-(1,2-dihydroxyethyl)phenol and 4-amino-2-(diethylaminomethyl)phenol.

Furthermore, the developer component can be selected from o-aminophenol and derivatives thereof, such as, for example, 2-amino-4-methylphenol, 2-amino-5-methylphenol or 2-amino-4-chlorophenol.

Furthermore, the developer component can be selected from heterocyclic developer components, such as, for example, from pyrimidine derivatives, pyrazole derivatives, pyrazolopyrimidine derivatives or physiologically tolerated salts thereof. Preferred pyrimidine derivatives are, in particular, the compounds 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine. Further suitable pyrazole derivatives are the compounds selected from 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, and physiologically tolerated salts thereof, but in particular 4,5-diamino-1-(2-hydroxyethyl)pyrazole. Suitable pyrazolopyrimidines are, in particular, pyrazolo[1,5-a]pyrimidines, where preferred pyrazolo[1,5-a]pyrimidines are selected from pyrazolo[1,5-a]pyrimidine-3,7-diamine, 2,5-dimethylpyrazolo[1,5-a]pyrimidine-3,7-diamine, pyrazolo[1,5-a]-pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo-[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 3-amino-7-dimethylamino-2,5-dimethylpyrazolo[1,5-a]pyrimidine and physiologically tolerated salts thereof and tautomeric forms thereof.

Further suitable developer components are selected from at least one compound from the group formed by p-phenylenediamine, p-tolylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,M-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxyl)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, and the physiologically tolerated salts of these compounds. Further suitable developer components here are p-tolylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole and physiologically tolerated salts thereof.

The developer components are preferably used in an amount of 0.0001 to 10% by weight, preferably 0.001 to 5% by weight, in each case based on the ready-to-use preparation or preparation component.

Suitable oxidation dye components of the coupler type are preferably selected from m-aminophenol and/or derivatives thereof, m-diaminobenzene and/or derivatives thereof, o-diaminobenzene and/or derivatives thereof, o-aminophenol and/or derivatives thereof, naphthalene derivatives containing at least one hydroxyl group, di- or trihydroxybenzene and/or derivatives thereof, pyridine derivatives, pyrimidine derivatives, monohydroxyindole derivatives and/or monoaminoindole derivatives, monohydroxyindoline derivatives and/or monoaminoindoline derivatives, pyrazolone derivatives, such as, for example, 1-phenyl-3-methylpyrazol-5-one, morpholine derivatives, such as, for example, 6-hydroxybenzo-morpholine or 6-aminobenzomorpholine, quinoxaline derivatives, such as, for example, 6-methyl-1,2,3,4-tetrahydroquinoxaline, and/or mixtures of two or more compounds from one or more of these classes.

Further coupler components which can be used, such as m-aminophenols or derivatives thereof, are preferably selected from at least one compound from the group formed by 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3-dihydroxy-5-(methylamino)benzene, 3-ethylamino-4-methylphenol, 2,4-dichloro-3-aminophenol and physiologically tolerated salts thereof.

Further coupler components which can be used, such as, for example, 3-diaminobenzenes or derivatives thereof, are preferably selected from at least one compound from the group formed by m-phenylenediamine, 2-(2,4-di-aminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino) ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxy-ethyl) aminobenzene and physiologically tolerated salts thereof.

Further coupler components which can be used, such as, for example, o-diaminobenzenes or derivatives thereof, are preferably selected from at least one compound from the group formed by 3,4-diaminobenzoic acid and 2,3-diamino-1-methylbenzene and physiologically tolerated salts thereof.

Further coupler components which can be used, such as, for example, di- or trihydroxybenzenes and derivatives thereof, are selected from at least one compound from the group formed by resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene.

Further coupler components which can be used, such as, for example, pyridine derivatives, are selected from at least one compound from the group formed by 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine and physiologically tolerated salts thereof. Naphthalene derivatives containing at least one hydroxyl group which are suitable as coupler component are selected from at least one compound from the group formed by 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene.

Indole derivatives which are suitable as coupler component are selected from 4-hydroxyindole, 6-hydroxyindole and 7-hydroxyindole and physiologically tolerated salts thereof.

Indoline derivatives which are suitable as coupler component are preferably selected from 4-hydroxyindoline, 6-hydroxyindoline and 7-hydroxyindoline and physiologically tolerated salts thereof.

Pyrimidine derivatives which are suitable as coupler component are selected from at least one compound from the group formed by 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine and physiologically tolerated salts thereof.

Suitable coupler components are selected from 3-aminophenol, 5-amino-2-methylphenol, 3-amino-2-chloro-6-methylphenol, 2-hydroxy-4-aminophenoxy-ethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethylamino]-2-methoxy-5-methylphenyl}amino) ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl) aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or physiologically tolerated salts thereof. Particular preference is given here to resorcinol, 2-methylresorcinol, 5-amino-2-methylphenol, 3-aminophenol, 2-(2,4-diaminophenoxyl)ethanol, 1,3-bis-(2,4-diaminophenoxyl)propane, 1-methoxy-2-amino-4-(2'-hydroxyethylamino)benzene, 2-amino-3-hydroxypyridine and 1-naphthol and one of the physiologically tolerated salts thereof.

The coupler components are preferably used in an amount of 0.0001 to 10% by weight, preferably 0.001 to 5% by weight, in each case based on the ready-to-use preparation or preparation component.

In the preparations described, which, in accordance with the invention, comprise a compound of formula I, I-a, I-b, I-c or I-d, coloured pigments may furthermore also be present, where the layer structure of the pigments is not limited.

The coloured pigment should preferably be skin-coloured or brownish in the case of the use of 0.5 to 5% by weight. The choice of a corresponding pigment is familiar to the person skilled in the art.

Besides the at least one compound of the formula I, I-a, I-b, I-c or I-d and any other ingredients, the preparations may comprise further organic UV filters, so-called hydrophilic or lipophilic sun-protection filters, which are effective in the UVA region and/or UVB region and/or IR and/or VIS region (absorbers). These substances can be selected, in particular, from cinnamic acid derivatives, salicylic acid derivatives, camphor derivatives, triazine derivatives, β,β-diphenylacrylate derivatives, p-aminobenzoic acid derivatives and polymeric filters and silicone filters, which are described in the application WO 93/04665. Further examples of organic and also inorganic UV filters are indicated in the patent applications EP-A 0 487 404 and WO2009/077356. The said UV filters are usually named below in accordance with INCI nomenclature.

Particularly suitable for a combination are:

para-aminobenzoic acid and derivatives thereof: PABA, Ethyl PABA, Ethyl dihydroxypropyl PABA, Ethylhexyl dimethyl PABA, for example marketed under the name "Escalol 507" by ISP, Glyceryl PABA, PEG-25 PABA, for example marketed under the name "Uvinul P25" by BASF.

Salicylates: Homosalate marketed by Merck under the name "Eusolex HMS"; Ethylhexyl salicylate, for example marketed by Symrise under the name "Neo Heliopan OS", Dipropylene glycol salicylate, for example marketed by Scher under the name "Dipsal", TEA salicylate, for example marketed by Symrise under the name "Neo Heliopan TS".

β,β-Diphenylacrylate derivatives: Octocrylene, for example marketed by Merck under the name "Eusolex® OCR", "Uvinul N539" from BASF, etocrylene, for example marketed by BASF under the name "Uvinul N35". Furthermore, for example, methoxycrylene, marketed by Hallstar under the name Solastay S1.

Benzophenone derivatives: Benzophenone-1, for example marketed under the name "Uvinul 400"; Benzophenone-2, for example marketed under the name "Uvinul D50"; Benzophenone-3 or Oxybenzone, for example marketed under the name "Uvinul M40"; Benzophenone-4, for example marketed under the name "Uvinul MS40"; Benzophenone-9, for example marketed by BASF under the name "Uvinul DS-49", Benzophenone-5, Benzophenone-6, for example marketed by Norquay under the name "Helisorb 11", Benzophenone-8, for example marketed by American Cyanamid under the name "Spectra-Sorb UV-24", Benzophenone-12 n-hexyl 2-(4-diethylamino-2-hydroxybenzoyl)benzoate or 2-hydroxy-4-methoxy-benzophenone, marketed by Merck, Darmstadt, under the name Eusolex® 4360.

Benzylidenecamphor derivatives: 3-Benzylidenecamphor, for example marketed under the name "Mexoryl SD" by Chimex, 4-Methylbenzylidenecamphor, for example marketed by Merck under the name "Eusolex 6300", benzylidenecamphorsulfonic acid, for example marketed by Chimex under the name "Mexoryl SL", Camphor benzalkonium methosulfate, for example marketed by Chimex under the name "Mexoryl SO", terephthalylidenedicamphorsulfonic acid, for example marketed by Chimex under the name "Mexoryl SX", Polyacrylamidomethylbenzylidenecamphor marketed by Chimex under the name "Mexoryl SW".

Phenylbenzimidazole derivatives: phenylbenzimidazolesulfonic acid, for example marketed by Merck under the name "Eusolex 232", disodium phenyl dibenzimidazole tetrasulfonate, for example marketed by Symrise under the name "Neo Heliopan AP".

Phenylbenzotriazole derivatives: Drometrizole trisiloxane, for example marketed by Rhodia Chimie under the name "Silatrizole", Methylenebis(benzo-triazolyl)tetramethylbutylphenol in solid form, for example marketed by Fairmount Chemical under the name "MIXXIM BB/100", or in micronised form as an aqueous dispersion, for example marketed by Ciba Specialty Chemicals under the name "Tinosorb M".

Triazine derivatives: Ethylhexyltriazone, for example marketed by BASF under the name "Uvinul T150", Diethylhexylbutamidotriazone, for example marketed by Sigma 3V under the name "Uvasorb HEB". Further triazine derivatives are by way of example 2,4,6-tris(diisobutyl 4'-aminobenzalmalonate)-s-triazine or 2,4,6-tris(biphenyl)-1,3,5-triazine, or butyl 4-({4-{[4-(butoxycarbonyl)phenyl]amino}-6-[(3-{1,3,3,3-tetramethyl-1-[(trimethylsilyl)oxy]disiloxanyl}propyl)amino]-1,3,5-triazin-2-yl}amino) benzoate, marketed under the name Mexoryl SBS. Structure of Mexoryl SBS:

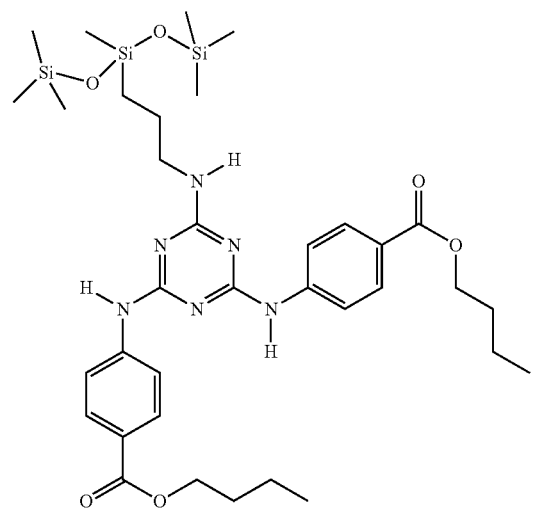

and bis-ethylhexyloxyphenol methoxyphenyl triazine, for example marketed by BASF under the name Tinosorb S.

Anthraniline derivatives: Menthyl anthranilate, for example marketed by Symrise under the name "Neo Heliopan MA".

Imidazole derivatives: ethylhexyldimethoxybenzylidenedioxoimidazoline propionate.

Benzalmalonate derivatives: polyorganosiloxanes containing functional benzalmalonate groups, such as, for example, polysilicone-15, for example marketed by Hoffmann LaRoche under the name "Parsol SLX".

4,4-Diarylbutadiene derivatives: 1,1-Dicarboxy(2,2'-dimethylpropyl)-4,4-diphenylbutadiene.

Benzoxazole derivatives: 2,4-bis[5-(1-dimethylpropyl)benzoxazol-2-yl(4-phenyl)imino]-6-(2-ethylhexyl)imino-1,3,5-triazine, for example marketed by Sigma 3V under the name Uvasorb K2A, and mixtures comprising this.

Piperazine derivatives, such as, for example, the compound

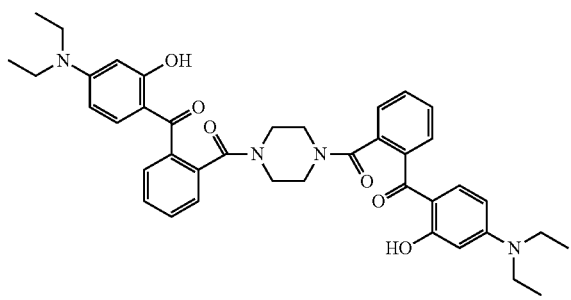 [SMILES: CCN(CC)c1ccc(C(=O)c2ccccc2C(=O)N2CCN(C(=O)c3ccccc3C(=O)c3ccc(N(CC)CC)cc3O)CC2)c(O)c1]

or the UV filters of the following structures

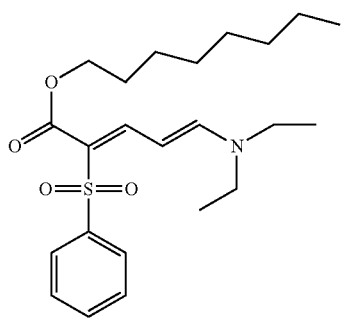

or

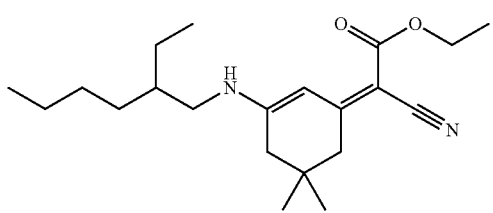

Preference is also given to a combination with UV filters based on polysiloxane copolymers having a random distribution in accordance with the following formula, where, for example, a=1.2; b=58 and c=2.8:

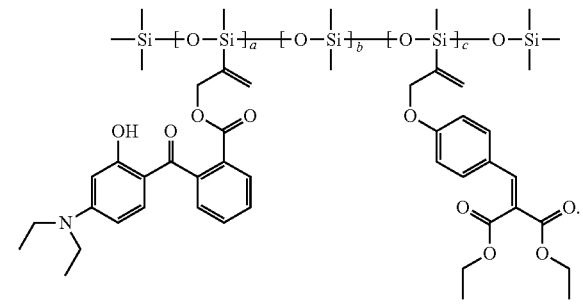

The compounds listed should only be regarded as examples. It is of course also possible to use other UV filters.

Suitable organic UV-protecting substances can preferably be selected from the following list: Ethylhexyl salicylate, Phenylbenzimidazolesulfonic acid, Benzophenone-3, Benzophenone-4, Benzophenone-5, n-Hexyl 2-(4-diethylamino-2-hydroxybenzoyl)benzoate, 4-Methylbenzylidenecamphor, Terephthalylidenedicamphorsulfonic acid, Disodium phenyldibenzimidazoletetrasulfonate, Methylenebis(benzotriazolyl)tetramethylbutylphenol, Ethylhexyl Triazone, Diethylhexyl Butamido Triazone, Drometrizole trisiloxane, Polysilicone-15, 1,1-Dicarboxy(2,2'-dimethylpropyl)-4,4-diphenylbutadiene, 2,4-Bis[5-(1-dimethylpropyl)benzoxazol-2-yl(4-phenyl)-imino]-6-(2-ethylhexyl)imino-1,3,5-triazine and mixtures thereof.

These organic UV filters are generally incorporated into formulations in an amount of 0.01 percent by weight to 20 percent by weight, preferably 1% by weight-10% by weight.

Besides the compounds of the formula I and any other organic UV filters, as described above, the preparations may comprise further inorganic UV filters, so-called particulate UV filters.

These combinations with particulate UV filters are possible both as a powder and also as a dispersion or paste of the following types.

Preference is given here both to those from the group of the titanium dioxides, such as, for example, coated titanium dioxide (for example Eusolex® T-2000, Eusolex® T-AQUA, Eusolex® T-AVO, Eusolex® T-OLEO), zinc oxides (for example Sachtotec®), iron oxides or also cerium oxides and/or zirconium oxides.

Furthermore, combinations with pigmentary titanium dioxide or zinc oxide are also possible, where the particle size of these pigments is greater than or equal to 200 nm, for example Hombitan® FG or Hombitan® FF-Pharma.

It may furthermore be preferred for the preparations to comprise inorganic UV filters which have been aftertreated by conventional methods, as described, for example, in Cosmetics & Toiletries, February 1990, Vol. 105, pp. 53-64. One or more of the following aftertreatment components can be selected here: amino acids, beeswax, fatty acids, fatty acid alcohols, anionic surfactants, lecithin, phospho-lipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerin.

Particulate UV filters which are preferably to be employed here are:

untreated titanium dioxides, such as, for example, the products Microtitanium Dioxide MT 500 B from Tayca; titanium dioxide P25 from Degussa, Aftertreated micronised titanium dioxides with aluminium oxide and silicon dioxide aftertreatment, such as, for example, the product "Microtitanium Dioxide MT 100 SA" from Tayca; or the product "Tioveil Fin" from Uniqema, Aftertreated micronised titanium dioxides with aluminium oxide and/or aluminium stearate/laurate aftertreatment, such as, for example, Microtitanium Dioxide MT 100 T from Tayca, Eusolex T-2000 from Merck, Aftertreated micronised titanium dioxides with iron oxide and/or iron stearate aftertreatment, such as, for example, the product "Microtitanium Dioxide MT 100 F" from Tayca, Aftertreated micronised titanium dioxides with silicon dioxide, aluminium oxide and silicone aftertreatment, such as, for example, the product "Microtitanium Dioxide MT 100 SAS" from Tayca, Aftertreated micronised titanium dioxides with sodium hexametaphosphates, such as, for example, the product "Microtitanium Dioxide MT 150 W" from Tayca.

The treated micronised titanium dioxides to be employed for the combination may also be aftertreated with:

octyltrimethoxysilanes; such as, for example, the product Tego Sun T 805 from Degussa, silicon dioxide; such as, for example, the product Parsol T-X from DSM, aluminium oxide and stearic acid; such as, for example, the product UV-Titan M160 from Sachtleben, aluminium and glycerin; such as, for example, the product UV-Titan from Sachtleben, aluminium and silicone oils, such as, for example, the product UV-Titan M262 from Sachtleben, sodium hexametaphosphate and polyvinylpyrrolidone, polydimethylsiloxanes, such as, for example, the product 70250 Cardre UF TiO2SI3 from Cardre, polydimethylhydrogenosiloxanes, such as, for example, the product Microtitanium Dioxide USP Grade Hydrophobic from Color Techniques.

The combination with the following products may furthermore also be advantageous:

Untreated zinc oxides, such as, for example, the product Z-Cote from BASF (Sunsmart), Nanox from Elementis Aftertreated zinc oxides, such as, for example, the following products:

ZnO aftertreated with polymethylhydrogenosiloxanes,

Nanogard Zinc Oxide FN from Nanophase Technologies

"SPD-Z1" from Shin-Etsu (ZnO aftertreated with a silicone-grafted acrylic polymer, dispersed in cyclodimethylsiloxanes)

"Escalol Z100" from ISP (aluminium oxide-aftertreated ZnO dispersed in an ethylhexyl methoxycinnamate/PVP-hexadecene/methicone copolymer mixture)

"Fuji ZNO-SMS-10" from Fuji Pigment (ZnO aftertreated with silicon dioxide and polymethylsilsesquioxane)

Untreated cerium oxide micropigment, for example with the name "Colloidal Cerium Oxide" from Rhone Poulenc Untreated and/or aftertreated iron oxides with the name Nanogar from Arnaud.

For example, it is also possible to employ mixtures of various metal oxides, such as, for example, titanium dioxide and cerium oxide, with and without aftertreatment, such as, for example, the product Sunveil A from Ikeda. In addition, it is also possible to use mixtures of aluminium oxide, silicon dioxide and silicone-aftertreated titanium dioxide, zinc oxide mixtures, such as, for example, the product UV-Titan M261 from Sachtleben, in combination with the UV protection agent according to the invention.

These inorganic UV filters are generally incorporated into the preparations in an amount of 0.1 percent by weight to 25 percent by weight, preferably 2% by weight-10% by weight.

By combination of one or more of the said compounds having a UV filter action, the protective action against harmful effects of the UV radiation can be optimised.

All said UV filters can also be employed in encapsulated form. In particular, it is advantageous to employ organic UV filters in encapsulated form. It may therefore be preferred for one or more of the above-mentioned UV filters to be in encapsulated form. It is advantageous here for the capsules to be so small that they cannot be observed with the naked eye. In order to achieve the above-mentioned effects, it is furthermore necessary for the capsules to be sufficiently stable and the encapsulated active compound (UV filter) only to be released to the environment to a small extent, or not at all.

Preferred preparations may also comprise at least one further cosmetic active compound, for example selected from antioxidants, anti-ageing active compounds, anti-cellulite active compounds, self-tanning substances, skin-lightening active compounds or vitamins.

Dyes according to the invention can furthermore be combined with all active compounds and assistants as listed systematically in WO2009/098139. In particular, these substances belong to the use categories mentioned therein "moisturisers and humectants", "desquamating agents", "agents for improving the barrier function", "depigmenting agents", "antioxidants", "dermo-relaxing or dermo-decontracting agents", "anti-glycation agents", "agents for stimulating the synthesis of dermal and/or epidermal macromolecules and/or for preventing their degradation", "agents for stimulating fibroblast or keratinocyte proliferation and/or keratinocyte differentiation", "agents for promoting the maturation of the horny envelope", "NO-synthase inhibitors", "peripheral benzodiazepine receptor (PBR) antagonists", "agents for increasing the activity of the sebaceous glands", "agents for stimulating the energy metabolism of cells", "tensioning agents", "fat-restructuring agents", "sliming agents", "agents for promoting the cutaneous microcirculation", "calmatives or anti-irritants", "seboregulating or anti-seborrhoic agents", "astringents", "cicatrising agents", "anti-inflammatory agents", "antiacne agents".

The protective action of preparations against oxidative stress or against the effect of free radicals can be improved if the preparations comprise one or more antioxidants, the person skilled in the art being presented with absolutely no difficulties in selecting antioxidants which act suitably quickly or with a time delay.

There are many proven substances known from the specialist literature which can be used as antioxidants, for example amino acids (for example glycine, histidine, tyrosine, tryptophan) and derivatives thereof, imidazoles, (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to µmol/kg), and also (metal) chelating agents, (for example α-hydroxyfatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate) and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, ZnSO$_4$), selenium and derivatives thereof (for example selenomethionine), stilbenes and derivatives thereof (for example stilbene oxide, trans-stilbene oxide).

Suitable antioxidants are also compounds of the formulae A or B

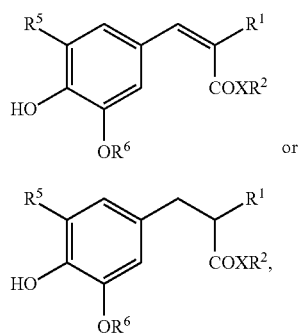

in which

R$^1$ can be selected from the group —C(O)CH$_3$, —CO$_2$R$^3$, —C(O)NH$_2$ and —C(O)N(R$^4$)$_2$, X denotes O or NH, R$^2$ denotes linear or branched alkyl having 1 to 30 C atoms, R$^3$ denotes linear or branched alkyl having 1 to 20 C atoms, R$^4$ in each case, independently of one another, denotes H or linear or branched alkyl having 1 to 8 C atoms, R$^5$ denotes H or linear or branched alkyl having 1 to 8 C atoms or linear or branched alkoxy having 1 to 8 C atoms and R$^6$ denotes linear or branched alkyl having 1 to 8 C atoms, preferably derivatives of 2-(4-hydroxy-3,5-dimethoxybenzylidene)malonic acid and/or 2-(4-hydroxy-3,5-dimethoxybenzyl)malonic acid, particularly preferably bis(2-ethylhexyl) 2-(4-hydroxy-3,5-dimethoxybenzylidene)malonate (for example Oxynex® ST Liquid) and/or bis(2-ethylhexyl) 2-(4-hydroxy-3,5-dimethoxybenzyl)malonate (for example RonaCare® AP).

Furthermore, the combination with bisisopropyl 2-(4-hydroxy-3-methoxy-benzylidene)malonate or bisisopropyl 2-(4-hydroxy-3-methoxybenzyl)malonate (hydrogenated diisopropyl vanilidene malonate) is preferred. An analogous situation applies to corresponding bisethyl esters.

Mixtures of antioxidants are likewise suitable for use in the cosmetic preparations according to the invention. Known and commercial mixtures are, for example, mixtures comprising, as active ingredients, lecithin, L-(+)-ascorbyl palmitate and citric acid, natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed in such compositions with the compounds according to the invention in percent by weight ratios in the range from 1000:1 to 1:1000, preferably in percent by weight ratios of 100:1 to 1:100.

Of the phenols which can be used in accordance with the invention, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential.

Quercetin (cyanidanol, cyanidenolon 1522, meletin, sophoretin, ericin, 3,3',4',5,7-pentahydroxyflavone) is frequently mentioned as a particularly effective antioxidant.

Suitable anti-ageing active compounds, in particular for skin-care preparations, are preferably so-called compatible solutes. These are substances which are involved in the osmoregulation of plants or microorganisms and can be isolated from these organisms. The generic term compatible solutes here also encompasses the osmolytes described in German patent application DE-A-10133202. Suitable osmolytes are, for example, the polyols, methylamine compounds and amino acids and respective precursors thereof. Osmolytes in the sense of German patent application DE-A-10133202 are taken to mean, in particular, substances from the group of the polyols, such as, for example, myo-inositol, mannitol or sorbitol, and/or one or more of the osmolytically active substances mentioned below: taurine, choline, betaine, phosphorylcholine, glycerophosphorylcholines, glutamine, glycine, α-alanine, glutamate, aspartate, proline, and taurine. Precursors of these substances are, for example, glucose, glucose polymers, phosphatidylcholine, phosphatidylinositol, inorganic phosphates, proteins, peptides and polyamino acids. Precursors are, for example, compounds which are converted into osmolytes by metabolic steps.

Compatible solutes which are preferably employed in accordance with the invention are substances selected from the group consisting of pyrimidinecarboxylic acids (such as ectoin and hydroxyectoin), proline, betaine, glutamine, cyclic diphosphoglycerate, N.-acetylornithine, trimethylamine N-oxide di-myo-inositol phosphate (DIP), cyclic 2,3-diphosphoglycerate (cDPG), 1,1-diglycerol phosphate (DGP), β-mannosyl glycerate (firoin), β-mannosyl glyceramide (firoin-A) or/and dimannosyl diinositol phosphate (DMIP) or an optical isomer, derivative, for example an acid, a salt or ester, of these compounds, or combinations thereof.

Of the pyrimidinecarboxylic acids, particular mention should be made here of ectoin ((S)-1,4,5,6-tetrahydro-2-methyl-4-pyrimidinecarboxylic acid) and hydroxyectoin ((S,S)-1,4,5,6-tetrahydro-5-hydroxy-2-methyl-4-pyrimidinecarboxylic acid) and derivatives thereof.

Anti-ageing active compounds which can be used are additionally products from Merck, such as, for example, 5,7-dihydroxy-2-methylchromone, marketed under the trade name RonaCare® Luremine, or the commercial products Ronacare® Isoquercetin, Ronacare® Tilirosid or Ronacare® Cyclopeptide 5.

Furthermore, the preparations according to the invention may comprise at least one self-tanning agent as further ingredient.

Advantageous self-tanning agents which can be employed are, inter alia: 1,3-dihydroxyacetone, glycerolaldehyde, hydroxymethylglyoxal, γ-dialdehyde, erythrulose, 6-aldo-D-fructose, ninhydrin, 5-hydroxy-1,4-naphtoquinone (juglone) or 2-hydroxy-1,4-naphtoquinone (lawsone). Very particular preference is given to 1,3-dihydroxyacetone, erythrulose or a combination thereof.

The preparations may also comprise one or more further skin-lightening active compounds or synonymously depigmentation active compounds. Skin-lightening active compounds can in principle be all active compounds known to the person skilled in the art. Examples of compounds having skin-lightening activity are hydroquinone, kojic acid, arbutin, aloesin, niacinamide, azelaic acid, elagic acid, tranexamic acid, potassium 4-methoxysalicylate, mulberry tree extract, magnesium ascorbyl phosphate, liquorice extract, emblica, ascorbic acid or rucinol, as well as substances as described under WO2007121845.

The preparations may comprise vitamins as further ingredients. Preference is given to vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active compound), thiamine (vitamin $B_1$), nicotinic acid (niacin), pyridoxine, pyridoxal, pyridoxamine, (vitamin $B_6$), panthothenic acid, biotin, folic acid and cobalamine (vitamin $B_{12}$), particularly preferably vitamin A palmitate, vitamin C and derivatives thereof, DL-α-tocopherol, tocopherol E acetate, nicotinic acid, pantothenic acid and biotin. In the case of cosmetic application, vitamins are usually added with the flavonoid-containing premixes or preparations in ranges from 0.01 to 5.0% by weight, based on the total weight. Nutrition-physiological applications are oriented towards the respective recommended vitamin requirement.

The retinoids described are at the same time also effective anti-cellulite active compounds. A likewise known anti-cellulite active compound is caffeine.

The said constituents of the preparation can be incorporated in the usual manner, with the aid of techniques which are well known to the person skilled in the art.

Suitable preparations are those for external application, for example can be sprayed onto the skin as cream or milk (O/W, W/O, O/W/O, W/O/W), as lotion or emulsion, in the form of oily-alcoholic, oily-aqueous or aqueous-alcoholic gels or solutions. They can be in the form of solid sticks or formulated as an aerosol. Administration forms such as capsules, dragees, powders, tablet solutions or solutions are suitable for internal use.

Examples which may be mentioned of application forms of the preparations to be employed are: solutions, suspensions, emulsions, PIT emulsions, pastes, ointments, gels, creams, lotions, powders, soaps, surfactant-containing cleansing preparations, oils, aerosols and sprays.

Preferred assistants originate from the group of preservatives, stabilisers, solubilisers, colorants, odour improvers.

Ointments, pastes, creams and gels may comprise the customary vehicles which are suitable for topical application, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary readily volatile, liquefied propellants, for example chlorofluorocarbons, propane/butane or dimethyl ether. Compressed air can also advantageously be used.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

A preferred solubiliser in general is 2-isopropyl-5-methylcyclohexanecarbonyl-D-alanine methyl ester.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkyl-amidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, powder make-up, emulsion make-up and wax make-up, and sunscreen, pre-sun and after-sun preparations.

The preferred preparation forms also include, in particular, emulsions.

Emulsions are advantageous and comprise, for example, the said fats, oils, waxes and other fatty substances, as well as water and an emulsifier, as usually used for a preparation of this type.

The lipid phase may advantageously be selected from the following group of substances:
mineral oils, mineral waxes
oils, such as triglycerides of capric or caprylic acid, furthermore natural oils, such as, for example, castor oil;
fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
silicone oils, such as dimethylpolysiloxanes, diethylpolysiloxanes, diphenylpolysiloxanes, and mixed forms thereof.

For the purposes of the present invention, the oil phase of the emulsions, oleogels or hydrodispersions or lipodispersions is advantageously selected from the group of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, from the group of esters of aromatic carboxylic acid and saturated and/or unsaturated, branched and/or unbranched alcohols having a chain length of 3 to 30 C atoms. Ester oils of this type can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The mixture according to the invention may preferably comprise assistants, such as, for example, cosmetic oils (for example Caprylic/Capric Triglycerides, C12-15 Alkyl Benzoate, isopropyl myristate, Arylalkyl Benzoate, such as, for example, phenethyl benzoate (X-Tend 226) or oil components of the Cosmacol brand, such as Dimyristyl Tartrate, Tri C14-C15 Alkyl Citrate, C12-C13 Alkyl Lactate, Tridecyl Salicylate, C12-C13 Alkyl Octanoate, C12-C13 Alkyl Malate, C12-C13 Alkyl Citrate, C12-C13 Alkyl Tartrate), or polar-protic assistants (for example propylene glycol, glycerine, isopropanol, ethanol) or so-called solubilisers (for example butylphthalimides, isopropylphthalimides, dimethylisosorbides).

The oil phase may furthermore advantageously be selected from the group of branched and unbranched hydrocarbons and hydrocarbon waxes, silicone oils, di-alkyl ethers, the group of saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18 C atoms. The fatty acid triglycerides may, for example, advantageously be selected from the group of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as sole lipid component of the oil phase.

The aqueous phase of the preparations to be employed optionally advantageously comprises alcohols, diols or polyols having a low carbon number, and ethers thereof, preferably ethanol, isopropanol, propylene glycol, glycerol, ethylene glycol, ethylene glycol monomethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

Emulsions are advantageous and comprise, for example, the said fats, oils, waxes and other fatty substances, as well as water and an emulsifier, as usually used for a formulation of this type.

In a preferred embodiment, the preparations to be employed comprise hydrophilic surfactants. The hydrophilic surfactants are preferably selected from the group of the alkylglucosides, acyl lactylates, betaines and coconut amphoacetates.

It is likewise advantageous to employ natural or synthetic raw materials and assistants or mixtures which are distinguished by an effective content of the active compounds used in accordance with the invention, for example Plantaren® 1200 (Henkel KGaA), Oramix® NS 10 (Seppic).

The cosmetic and dermatological preparations may exist in various forms. Thus, they may be, for example, a solution, a water-free preparation, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer ectoins in encapsulated form, for example in collagen matrices and other conventional encapsulation materials, for example as cellulose encapsulations, in gelatine, wax matrices or liposomally encapsulated. In particular, wax matrices, as described in DE-A-43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions.

The co-emulsifiers selected are advantageously, for example, O/W emulsifiers, principally from the group of substances having HLB values of 11-16, very particularly advantageously having HLB values of 14.5-15.5, so long as the O/W emulsifiers have saturated radicals R and R'. If the O/W emulsifiers have unsaturated radicals R and/or R', or if isoalkyl derivatives are present, the preferred HLB value of such emulsifiers may also be lower or higher.

It is advantageous to select the fatty alcohol ethoxylates from the group of the ethoxylated stearyl alchols, cetyl alcohols, cetylstearyl alcohols (cetearyl alcohols).

It is furthermore advantageous to select the fatty acid ethoxylates from the following group:
polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13)isostearate, polyethylene glycol (14)isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24)isostearate, polyethylene glycol (25)isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth1-4 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/cprinate, polyethylene glycol (20) glyceryl oleate, polyethylene glycol (20) glyceryl isostearate, polyethylene glycol (18) glyceryl oleate (cocoate).

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be employed as optional W/O emulsifiers, but ones which may nevertheless be advantageous in accordance with the invention:

fatty alcohols having 8 to 30 carbon atoms, monoglycerol esters of saturated and/or unsaturated, branched and/or unbranched alkanecarboxylic acids having a chain length of 8 to 24, in particular 12-18 C atoms, diglycerol esters of saturated and/or unsaturated, branched and/or unbranched alkanecarboxylic acids having a chain length of 8 to 24, in particular 12-18 C atoms, monoglycerol ethers of saturated and/or unsaturated, branched and/or unbranched alcohols having a chain length of 8 to 24, in particular 12-18 C atoms, diglycerol ethers of saturated and/or unsaturated, branched and/or unbranched alcohols having a chain length of 8 to 24, in particular 12-18 C atoms, propylene glycol esters of saturated and/or unsaturated, branched and/or unbranched alkanecarboxylic acids having a chain length of 8 to 24, in particular 12-18 C atoms, and sorbitan esters of saturated and/or unsaturated, branched and/or unbranched alkanecarboxylic acids having a chain length of 8 to 24, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate or PEG-30 dipolyhydroxystearate.

The preparation may comprise cosmetic adjuvants which are usually used in this type of preparation, such as, for example, thickeners, softeners, moisturisers, surface-active agents, emulsifiers, preservatives, antifoams, perfumes, waxes, lanolin, propellants, dyes and/or pigments, and other ingredients usually used in cosmetics.

The dispersant or solubiliser used can be an oil, wax or other fatty substance, a lower monoalcohol or a lower polyol or mixtures thereof. Particularly preferred monoalcohols or polyols include ethanol, i-propanol, propylene glycol, glycerol and sorbitol.

A preferred embodiment of the invention is an emulsion which is in the form of a protective cream or milk and comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The preparation may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a preparation is formulated as an aerosol, use is generally made of the customary propellants, such as alkanes, fluoroalkanes and chlorofluoroalkanes, preferably alkanes.

Even without further comments, it is assumed that a person skilled in the art will be able to utilise the above description in the broadest scope. The preferred embodiments and examples should therefore merely be regarded as descriptive disclosure which is absolutely not limiting in any way. The complete disclosure content of all applications and publications mentioned above and below is incorporated into this application by way of reference. The percent by weight ratios of the individual ingredients in the preparations of the examples expressly belong to the disclosure content of the description and can therefore be utilised as features.

Further important features and advantages of the invention arise from the sub-claims and from the examples.

It goes without saying that the features mentioned above and still to be explained below can be used not only in the respective combination indicated, but also in other combinations or in isolation without leaving the context of the present invention.

Preferred embodiments of the invention are described in the examples and are explained in greater detail in the following description without restricting the scope of the present invention.

EXAMPLES

Example 1

Preparation of 2-methyl-4-oxo-4H-pyran-3-yl 4-phenylazo-benzoate

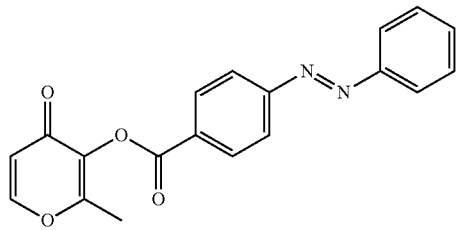 [SMILES: Cc1occc(=O)c1OC(=O)c1ccc(/N=N/c2ccccc2)cc1]

5.20 g (23.0 mmol) of 4-(phenylazo)benzoic acid and 3.50 g (27.8 mmol) of 3-hydroxy-2-methyl-4-pyranone are suspended in 50 ml of THF together with 0.28 g (2.30 mmol) of 4-(dimethylamino)pyridine. A solution of 5.70 g (27.6 mmol) of N, N'-dicyclohexylcarbodiimide in 10 ml of THF is added dropwise to the red suspension. A temperature increase from 22° C. to 30° C. is observed during this operation. The reaction mixture thickens. The mixture is stirred at room temperature (RT) for a further 48 h. 2.50 g (27.8 mmol) of oxalic acid dihydrate are then added, and the mixture is stirred at RT for a further 2.5 h. After cooling to 0° C., the mixture is filtered, and the filter cake is rinsed with 50 ml of THF. The filter cake is extracted by stirring with 150 ml of THF and filtered off with suction again. The combined washing solutions are concentrated to about 150 ml. Red crystals are obtained therefrom overnight at RT, which are then rinsed with a little ethyl acetate and then dried in vacuo. Product weight: 2.25 g. (29% of theory)

$^1$H-NMR (400 MHz, DMSO-$d_6$): δ=2.36 (s, 3H), 6.54 (d, $^3$J=5.7 Hz, 1H), 7.68 (m, 3H), 8.00 (m, 2H), 8.10 (m, 2H), 8.27 (d, $^3$J=5.8 Hz, 1H), 8.35 (m, 2H).

Example 2

Preparation of 2-methyl-4-oxo-4H-pyranyl 4-(4-dimethylamino-phenylazo)benzoate

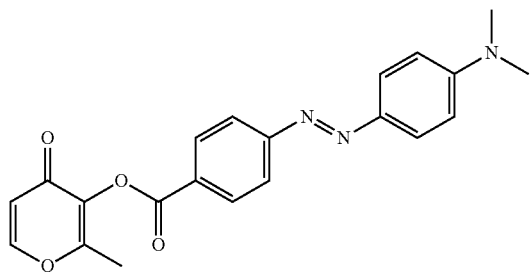 [SMILES: Cc1occc(=O)c1OC(=O)c1ccc(/N=N/c2ccc(N(C)C)cc2)cc1]

0.32 g (2.60 mmol) of 4-(dimethylamino)pyridine are added to a suspension of 3.90 g (30.9 mmol) of 3-hydroxy-2-methyl-4-pyranone and 7.00 g (26.0 mmol) of 4-dimethylaminobenzene-4-carboxylic acid in 50 ml of THF. A solution of 6.40 g (31.0 mmol) of dicyclohexylcarbodiimide in 10 ml of THF is added dropwise over the course of 6 min. The red-brown suspension warms to 28° C. The mixture is stirred for a further 48 h, and 4.00 g (44.4 mmol) of oxalic acid dihydrate are then added. After stirring at RT for a further 2 h, the reaction mixture is cooled to 0° C., filtered, and the residue is rinsed with 70 ml of THF. 200 ml of ethyl acetate and 100 ml of water are added to the filtrate, the mixture is extracted, and the phases are separated. The organic phase is washed again with 55 ml of water, dried over sodium sulfate, filtered and evaporated in vacuo. The product is then recrystallised from isopropanol. After filtration with suction, the residue is stirred with 150 ml of THF, and the solid is filtered off with suction, the solid is then recrystallised again from 100 ml of acetonitrile and, if necessary, from isopropanol, giving a total of 280 mg.

$^1$H-NMR (400 MHz, DMSO-$d_6$): δ=2.34 (s, 3H), 3.20 (s, 6H), 6.53 (d, 1H), 6.88 (m, 2H), 7.84 (m, 2H), 7.95 (m, 2H), 8.24 (m, 3H).

Example 3

Preparation of 2-methyl-4-oxo-4H-pyran-3-yl 3-{4-[(E)-2-(4-dimethylamino-phenyl)vinyl]pyridin-1-yl}propionate

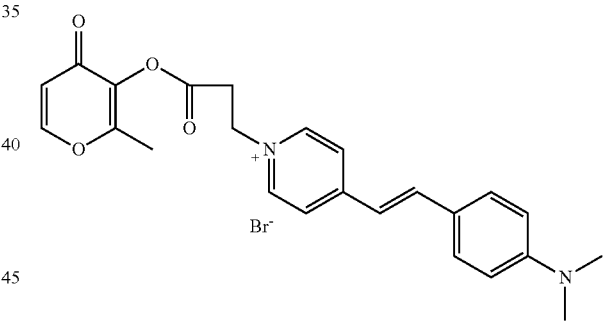

1.00 g (2.65 mmol) of E-1-(2-carboxyethyl)-4-(4-(dimethylamino)styryl)pyridinium bromide, 0.40 g (3.18 mmol) of 3-hydroxy-2-methyl-4-pyranone and 0.03 g (0.27 mmol) of 4-(dimethylamino)pyridine are suspended in 7 ml of THF under protective-gas atmosphere. 0.66 g (3.18 mmol) of N,N'-dicyclohexylcarbodiimide, dissolved in 3 ml of THF, are added dropwise to the red suspension at RT, and stirring is continued overnight. 0.29 g (3.18 mmol) of oxalic acid dihydrate are then added, and the mixture is stirred for a further 72 hours. 15 ml of THF are then added, and the mixture is stirred for a further 1 hour. The mixture is filtered in vacuo, and the residue is rinsed with 10 ml of THF. The mother liquor is evaporated in vacuo in a rotary evaporator, and 15 ml of ethyl acetate are added to the red solid obtained. The mixture is filtered in vacuo, and the solid is rinsed with ethyl acetate, giving 750 mg of solid, which are eluted with 10 ml of MeOH on 15 g of silica gel. Removal of the solvent gives 80 mg of red amorphous solid ($R_f$=0.07; MeOH).

Example 4

Synthesis of 6-[6-(3-dimethylaminopropylamino)-1,3-dioxo-1H,3H-benzo[de]-isoquinolin-2-yl]hexanoic acid 2-methyl-4-oxo-4H-pyran-3-yl ester (4)

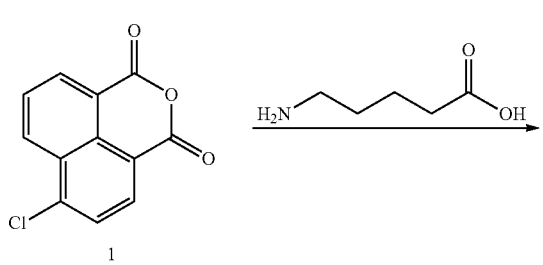

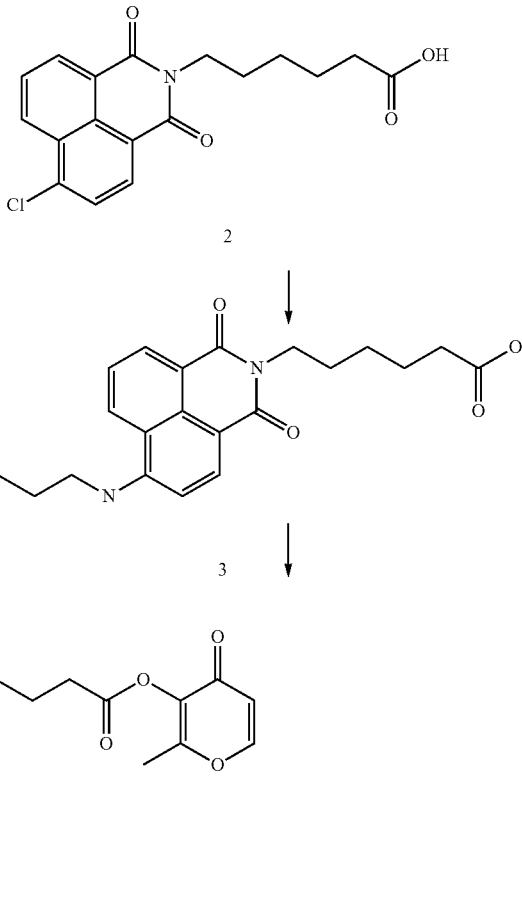

Compound 3 is prepared by converting commercially available 6-chlorobenzo[de]-isochromene-1,3-dione by the method of W. Adam et al, *Tetrahedron: Asymmetry* 2003, 14(10), 1355-1361 into compound 2, which is aminated correspondingly by the method described in U.S. Pat. No. 5,235,045 A to give compound 3. The reaction of the free acid of compound 3 with 3-hydroxy-2-methyl-4-pyranone is carried out analogously to Example 1.

Example 5

Preparation of 1,2-dimethyl-4-oxo-1,4-dihydropyridin-3-yl 4-phenylazo-benzoate

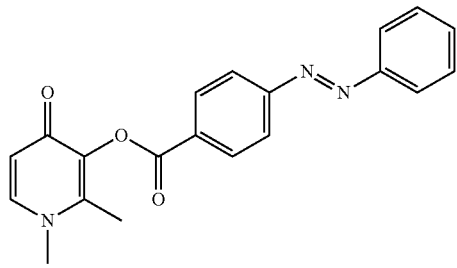 [SMILES: Cc1c(OC(=O)c2ccc(/N=N/c3ccccc3)cc2)c(=O)ccn1C]

1,2-Dimethyl-4-oxo-1,4-dihydropyridin-3-yl 4-phenylazobenzoate is prepared analogously to Example 1 using 3-hydroxy-1,2-dimethyl-1H-pyridin-4-one as starting material instead of 3-hydroxy-2-methyl-4-pyranone.

Example 6

Determination of the Protein Affinity in the Lysine Model

In each case, 10 mg of the substances from Example 1 and 2 are weighed out into a 10 ml volumetric flask and dissolved in 5 ml of tetrahydrofuran (THF). The volumetric flask is then made up to the mark with a lysine solution in distilled water. The concentration of the lysine solution is 200 mg/l of water. The solution is stirred in the volumetric flask at 35° C. for 24 h. Samples are taken after 1 h and after 24 h. 5 µl of each of these samples are pipetted onto the start zone of an HPTLC silica gel 60 F245 plate (Merck Art. 1.05628) using a micropipette. For development of the HPTLC plate, the eluent consisting of THF/heptane in the ratio 75/25 containing 0.1 vol % of formic acid is used. After development, detection is carried out at 254 nm and 366 nm in a CAMAG ATS4, and the Rf values are determined.

Result: substance 1 has an Rf value of 0.62, substance 2 has an Rf value of 0.57. After only 1 h in combination with lysine, both substances have reacted substantially, after 24 h completely, with lysine in a protein reaction. The starting substances can no longer be detected. By contrast, Maillard products have formed which are detected in the start zone of the HPTLC plate.

Example 7

Textile Colouring

The substances according to Example 1 and Example 2 are dissolved/dispersed in water to the extent of 5% each. The pH of the water is alkaline. The aqueous solution/dispersion is firstly boiled and subsequently cooled slowly to below 40° C., before the wool is added (about 1 kg of wool per 25-30 liters of water). After 24 h, the wool is removed and rinsed well with tap water.

Example A

Hair Dye Comprising Various Components

Component A:
Tocopherol, Linalool, Geraniol, Disodium EDTA, perfume, ascorbic acid, alcohol denat., Sodium sulfite, Sodium hydroxide, Sodium cocoyl isethionate, Bis-ethylhexyl Hydroxydimethoxy Benzylmalonate, Sodium lauryl sulfate, Ammonia, Lanolin alcohol, Glycol distearate, Sodium laureth sulfate, Glyceryl stearate, Cetearyl alcohol, Aqua.

Component B:
Aqua, hydrogen peroxide, cetearyl alcohol, PPG-38-buteth-37, petrolatum, laureth-2, sodium cetearyl sulfate, salicylic acid, disodium phosphate, phosphoric acid, etidronic acid.

Component C:
Ethanolic solution of the dyes according to Example 2 and/or 3 (2% by weight each) additionally containing Bis-ethylhexyl Hydroxydimethoxy Benzylmalonate (1% by weight).

Component D:
Ethanolic solution of Bis-ethylhexyl Hydroxydimethoxy Benzylmalonate (1% by weight).

Use:
For hair colouring, the following procedure is preferably followed in the following sequence: firstly, the hair is pretreated with component C, components B and C are subsequently mixed and applied to the hair. When the colouring is complete, component D is applied.

Example B

Hair Dye Comprising Various Components

Component A:
Tocopherol, Linalool, Geraniol, Disodium EDTA, perfume, Toluene-2,5-diamine sulfate, ascorbic acid, alcohol denat., Sodium sulfite, Sodium hydroxide, Sodium cocoyl isethionate, Bis-ethylhexyl Hydroxydimethoxy Benzylmalonate, 2-Methylresorcinol, 6-Amino-m-cresol, 4-Amino-2-hydroxy-toluene, 4-Amino-m-cresol, Sodium lauryl sulfate, Ammonia, Lanolin alcohol, Glycol distearate, Sodium laureth sulfate, Glyceryl stearate, Cetearyl alcohol, Aqua.

Component B:
Aqua, hydrogen peroxide, cetearyl alcohol, PPG-38-buteth-37, petrolatum, laureth-2, sodium cetearyl sulfate, salicylic acid, disodium phosphate, phosphoric acid, etidronic acid.

Component C:
Ethanolic solution of the dye according to Example 1 and/or Example 2, 3 or 4 (2% by weight each) additionally containing Bis-ethylhexyl Hydroxydimethoxy Benzylmalonate (1% by weight).

Component D:
Ethanolic solution of Bis-ethylhexyl Hydroxydimethoxy Benzylmalonate (1% by weight).

Use:
For hair colouring, the following procedure is preferably followed in the following sequence: firstly, the hair is pretreated with component C, components B and C are subsequently mixed and applied to the hair. When the colouring is complete, component D is applied.

All illustrative formulations of the compositions can optionally also be prepared without UV filters.

Example C

W/O Emulsion

| | a | b | c | d | e |
|---|---|---|---|---|---|
| Cetyl PEG/PPG-10/1 dimethicone (Abil EM 90) | 3.00 | 3.00 | 3.00 | 3.00 | 3.00 |
| Polyglyceryl-4 isostearate (Isolan GI 34) | 1.50 | 1.50 | 1.50 | 1.50 | 1.50 |
| Butylphthalimide isopropylphthalimide (Pelemol ® BIP) | 5.00 | 5.00 | 5.00 | 5.00 | 5.00 |
| Dimethyl isosorbide (Arlasolve DMI) | 5.00 | 5.00 | 5.00 | 5.00 | 5.00 |
| Dye according to Example 1 | 2.00 | | | | 1.00 |
| Dye according to Example 2 | | 2.00 | | | 1.00 |
| Dye according to Example 3 | | | 2.00 | | 1.00 |
| Dye according to Example 4 | | | | 2.00 | 1.00 |
| Uvinul ® A Plus (DHHB) | | 1.00 | 1.00 | 1.00 | |
| Ascorbic acid | | | 0.37 | 1.00 | 3.00 |
| Mineral Oil | 8.00 | 8.00 | 8.00 | 8.00 | 8.00 |
| Ethylhexyl stearate (Tegosoft ® OS) | 5.00 | 5.00 | 5.00 | 5.00 | 5.00 |
| Cyclomethicone (and) Aluminium/Magnesium Hydroxide Stearate (Gilugel SIL 5) | 5.00 | 5.00 | 5.00 | 5.00 | 5.00 |
| Preservative | 1.00 | 1.00 | 1.00 | 1.00 | 1.00 |
| Water | To 100 | To 100 | To 100 | To 100 | To 100 |
| NaCl | 0.50 | 0.50 | 0.50 | 0.50 | 0.50 |
| EDTA | 0.10 | 0.10 | 0.10 | 0.10 | 0.10 |
| Citric acid q.S. | | | | | |

Preparation:
Pelemol® BIP, Arlasolv DMI and emulsifiers are initially introduced. The dyes of Examples 1 to 4 and Uvinul® A Plus are dissolved therein. The remaining constituents of the oil phase are added and mixed homogeneously. The water phase, adjusted to pH=4-5 using citric acid, is emulsified in with stirring. The mixture is subsequently homogenised. The emulsions can be prepared under gentle conditions at room temperature.

Example D

Water-Resistant Sunscreen Spray with Application Control

A

| | | | |
|---|---|---|---|
| Dye according to Example 1, 2, 3 or 4 | 1.00 | 1.00 | 2.00 |
| Diethylhexyl Syringylidenemalonate, Caprylic/Capric Triglyceride (Oxynex ® ST Liquid) | | 0.50 | |
| RonaCare ® AP | | 2.00 | |
| Ascorbyl Palmitate | | | 1.00 |
| Cyprylic/capric Triglyceride (Miglyol 812N) | 7.00 | 7.00 | 7.00 |
| Butylphthalimide isopropylphthalimide (Pelemol ® BIP) | 9.00 | 9.00 | 9.00 |
| C12-15 alkyl benzoate (Tegosoft ® TN) | 10.00 | 10.00 | 10.00 |
| Phenethyl benzoate (X-Tend 226) | 5.00 | 5.00 | 5.00 |
| RonaCare ® tocopherol acetate | 1.00 | 1.00 | 1.00 |

B

| | | | |
|---|---|---|---|
| Cyclopentasiloxane (Dow Corning 245) | 43.80 | 41.30 | 41.80 |
| Phenyltrimethicone (Dow Corning 556) | 2.00 | 2.00 | 2.00 |
| Cyclopentasiloxane, dimethiconol Dow Corning 1501 Fluid | 20.00 | 20.00 | 20.00 |
| Perfume oil (q.s.) | 0.20 | 0.20 | 0.20 |

Preparation: the components of phase A are combined at room temperature and stirred until a clear solution or homogeneous dispersion is present. Phase B is subsequently mixed and added to phase B with stirring. Stirring is continued until the homogeneous product is finally present. To addition of antioxidants, such as Oxynex® ST Liquid, RonaCare® AP or ascorbyl palmitate, the stability of the substances according to the invention can be increased.

Example E

Pump Hair-Tinting Spray

A

| | | | |
|---|---|---|---|
| Dye according to Example 1 | 1.00 | 1.00 | 4.00 |
| Dye according to Example 2 | 1.00 | | |
| Dye according to Example 3 | | 1.00 | |
| Dye according to Example 4 | | | 1.00 |
| Ethanol 96% extra pure | To 100 | To 100 | To 100 |
| PVP/VA copolymer PVP/VA W 735 | 6.00 | 6.00 | 6.00 |

B

| | | | |
|---|---|---|---|
| Diethylhexyl Syringylidenemalonate, Caprylic/Capric Triglyceride (Oxynex ® ST Liquid) | 0.06 | 0.25 | 0.50 |
| PEG-75 Lanolin | 0.20 | 0.20 | 0.20 |
| BHT (Solan E-Low Dioxane) | | | |
| Perfume (Frag 280853 Green Activating) | 0.10 | 0.10 | 0.10 |

C

| | | | |
|---|---|---|---|
| Water, demineralised | 13.00 | 13.00 | 13.00 |
| Titriplex III | 0.10 | 0.10 | 0.10 |
| PEG-12 dimethicone Dow Corning 193 Fluid | 0.50 | 0.50 | 0.50 |
| 0.1% D&C Red No 33 (CI 17200) in water | 0.20 | 0.20 | 0.20 |
| PEG-40 Hydrogenated Castor Oil (Cremophor RH 410) | 1.00 | 1.00 | 1.00 |

Preparation: pre-dissolve phase A until a clear solution is present. Add phase B to phase A with stirring. Pre-mix phase C and add to the remainder, stir until a homogeneous mixture has formed.

Example F

W/O Emulsions

| Emulsion | A | B | C | D | E | F |
|---|---|---|---|---|---|---|
| Polyglyceryl 2-dipolyhydroxystearate | 3 | 5 | 3 | | | |
| PEG-30 dipolyhydroxystearate | | | 2 | 3 | 4 | 5 |
| Sodium starch octenylsuccinate | 0.5 | 0.4 | | 0.3 | | 1 |
| Glycine | 0.3 | 0.3 | 0.5 | 0.4 | | |
| Alcohol | | 5 | 2 | 5 | 4 | |
| Magnesium sulfate | 0.2 | 0.3 | 0.3 | 0.4 | 0.5 | 0.2 |
| $C_{12-15}$ Alkyl benzoate | 5 | 3 | | | 5 | |
| $C_{12-13}$ Alkyl tartrate | | 2 | | | | |
| Butylene glycol dicaprylate/dicaprate | 5 | | | | 3 | 3 |
| Dicaprylyl Ether | | | | | 2 | |
| Mineral oil | | 4 | | 6 | | 8 |
| Octyldodecanol | 2 | | | | | |
| Dicapryl caprate | | 2 | | | 2 | 2 |
| Cyclomethicone | 5 | | 5 | 10 | | |
| Dimethicone | | | | 5 | | |
| Isohexadecane | | 1 | | | | |
| Butylene glycol | 5 | 8 | | | | 3 |
| Propylene glycol | | | 1 | | 5 | 3 |
| Glycerine | 3 | 5 | 7 | 10 | 3 | 3 |
| C18-38 acid triglycerides | 0.5 | | 1 | | 1 | |
| Titanium dioxide | 5 | 6 | 4 | | | 4 |
| Zinc oxide | 5 | | | | | |
| Bis-ethylhexyloxyphenol methoxyphenyltriazine | | 3 | 3 | 2 | | |
| Ethylhexyltriazone | | 4.5 | 3 | | 3 | |
| Dye A | 1.0 | | 1.5 | 1.0 | 3.0 | |
| Diethylhexylbutamidotriazone | | | 1.5 | 4 | | |
| Butylmethoxydibenzoylmethane | 2 | 3 | 4 | | 1 | 3 |
| Uvinul ® A Plus | | | | 4 | 2 | |
| Ethylhexyl methoxycinnamate | | | | | 7 | 5 |
| Dye according to Example 2 | | 4.0 | 0.5 | 1.5 | | 0.5 |
| Taurine | 0.1 | | | 0.5 | 0.2 | |
| Vitamin E acetate | 0.2 | 02 | | 0.3 | 0.1 | 0.5 |
| $Na_2H_2EDTA$ | 0.1 | 0.1 | 0.2 | 0.2 | 0.2 | 0.5 |
| C8-C16 alkylpolyglycoside | 1 | | | | | |
| Perfume, preservative | q.s. | q.s | q.s. | q.s | qs. | qs. |
| Dyes, etc. | q.s. | q.s. | q.s. | q.s | q.s. | q.s. |
| Sodium hydroxide | q.s. | q.s. | q.s. | q.s | q.s. | q.s. |
| Water | to 100.0 | to 100.0 | to 100.0 | to 100.0 | to 100.0 | to 100.0 |

Example G

Hair-Care Formulation

| Component | Content in g of component per 100 g of formulation | | | | | |
|---|---|---|---|---|---|---|
| | A | B | C | D | E | F |
| Disodium EDTA | 0.100 | 0.100 | 0.100 | 0.100 | 0.100 | 0.100 |
| Oxynex ®ST | 2.000 | 2.000 | 2.000 | 2.000 | 2.000 | 2.000 |
| Dye according to Example 1 | 0.10 | 0.25 | 0.50 | 1.50 | 2.00 | 4.00 |
| Dye according to Example 2 | 0.50 | 1.00 | 1.50 | 2.00 | 2.50 | 3.00 |
| Hexamidine diisethionate | 0.100 | 0 | 0 | 0 | 0 | 0 |
| Tetrahydrocurcumin | 0 | 0.500 | 0 | 0 | 0 | 0 |
| Glycyrrhetinic acid | 0 | 0 | 0.300 | 0 | 0 | 0 |
| Thiotaine ®[1] | 0 | 0 | 0 | 5.000 | 0 | 0 |
| N-Undecylenoyl-L-phenylalanine | 0 | 0 | 0 | 0 | 1.000 | 0 |
| N-Acetyl glucosamine | 0 | 0 | 0 | 0 | 0 | 2.000 |
| Niacinamide | 5.000 | 5.000 | 5.000 | 5.000 | 5.000 | 5.000 |
| Citric acid | 0.015 | 0 | 0 | 0 | 0 | 0 |
| Isohexadecane | 3.000 | 3.000 | 3.000 | 3.000 | 3.000 | 3.000 |
| Isopropyl isostearate | 1.330 | 1.330 | 1.330 | 1.330 | 1.330 | 1.330 |
| Isopropyl N-laurosylsarcosinate | 0 | 0 | 5.000 | 0 | 0 | 0 |
| Sucrose polycottonseedate | 0.670 | 0.670 | 0.670 | 0.670 | 0.670 | 0.670 |
| Polymethylsilsesquioxane | 0.250 | 0.250 | 0.250 | 0.250 | 0.250 | 0.250 |
| Cetearyl glucoside + cetearyl alcohol | 0.200 | 0.200 | 0.200 | 0.200 | 0.200 | 0.200 |
| Behenyl alcohol | 0.400 | 0.400 | 0.400 | 0.400 | 0.400 | 0.400 |
| Ethylparaben | 0.200 | 0.200 | 0.200 | 0.200 | 0.200 | 0.200 |
| Propylparaben | 0.100 | 0.100 | 0.100 | 0.100 | 0.100 | 0.100 |
| Cetyl alcohol | 0.320 | 0.320 | 0.320 | 0.320 | 0.320 | 0.320 |
| Stearyl alcohol | 0.480 | 0.480 | 0.480 | 0.480 | 0.480 | 0.480 |
| Tocopheryl acetate | 0.500 | 0.500 | 0.500 | 0.500 | 0.500 | 0.500 |
| PEG-100 stearate | 0.100 | 0.100 | 0.100 | 0.100 | 0.100 | 0.100 |
| Glycerine | 7.000 | 7.000 | 7.000 | 7.000 | 7.000 | 7.000 |
| Titanium dioxide | 0.604 | 0.604 | 0.604 | 0.604 | 0.604 | 0.604 |
| Polyacrylamide + C13-14 isoparaffin + laureth-7 | 3.000 | 2.000 | 2.000 | 2.000 | 2.000 | 2.000 |
| Panthenol | 1.000 | 1.000 | 1.000 | 1.000 | 1.000 | 1.000 |
| Benzyl alcohol | 0.400 | 0.400 | 0.400 | 0.400 | 0.400 | 0.400 |
| Dimethicone + dimethiconol | 2.000 | 2.000 | 2.000 | 2.000 | 2.000 | 2.000 |
| Water (to 100 g) | to 100 | to 100 | to 100 | to 100 | to 100 | to 100 |
| TOTAL | 100 | 100 | 100 | 100 | 100 | 100 |

Example H

Hair-Care Formulation

| Component | Content in g of component per 100 g of formulation | | |
|---|---|---|---|
| | G | H | I |
| Disodium EDTA | 0.100 | 0.100 | 0.100 |
| Oxynex ® ST | 2.000 | 2.000 | 2.000 |
| Dye according to Example 1, 2, 3 or 4 or dye combination of the dyes according to Example 1, 2, 3 and/or 4 | 0.20 | 1.500 | 0.75 |
| Cetyl pyridinium chloride | 0.200 | 0 | 0 |
| Pitera ® | 0 | 10 | 0 |
| Ascorbyl glycoside | 0 | 0 | 2.000 |
| Niacinamide | 3.500 | 5.000 | 4.000 |
| Polyquaternium 37 | 0 | 0 | 0 |
| Isohexadecane | 3.000 | 2.500 | 2.000 |
| Isopropyl isostearate | 1.330 | 1.330 | 1.330 |
| Sucrose polycottonseedate | 0.670 | 0.670 | 0.670 |
| Polymethylsilsesquioxane | 0.250 | 0.250 | 0.250 |
| Cetearyl glucoside + cetearyl alcohol | 0.200 | 0.200 | 0.200 |
| Behenyl alcohol | 0.400 | 0.400 | 0.400 |
| Ethylparaben | 0.200 | 0.200 | 0.200 |
| Propylparaben | 0.100 | 0.100 | 0.100 |
| Cetyl alcohol | 0.320 | 0.320 | 0.320 |
| Stearyl alcohol | 0.480 | 0.480 | 0.480 |
| Tocopheryl acetate | 0.500 | 0.500 | 0.500 |
| PEG-100 stearate | 0.100 | 0.100 | 0.100 |
| Glycerine | 7.000 | 7.000 | 7.000 |
| Titanium dioxide | 0.604 | 0.604 | 0.604 |
| Polyacrylamide + C13-14 isoparaffin + laureth-7 | 2.000 | 2.000 | 2.000 |
| Panthenol | 1.000 | 1.000 | 1.000 |
| Benzyl alcohol | 0.400 | 0.400 | 0.400 |
| Dimethicone + dimethiconol | 2.000 | 2.000 | 2.000 |
| Water (to 100 g) | to 100 | to 100 | to 100 |
| TOTAL | 100 | 100 | 100 |

Example I

O/W Emulsions

| Emulsion | A | B | C | D | E | F |
|---|---|---|---|---|---|---|
| Glyceryl stearate citrate | 2.5 | 2 | 3 | | | |
| Sorbitan stearate | 0.5 | | | 2 | 1.5 | 2 |
| Polyglyceryl-3 methylglycose distearate | | | | 2.5 | 3 | 3 |

-continued

| Emulsion | A | B | C | D | E | F |
|---|---|---|---|---|---|---|
| Polyglyceryl-2 dipolyhydroxystearate | | 0.8 | | | | 0.5 |
| Cetearyl alcohol | | | 1 | | | |
| Stearyl alcohol | 2 | | | | | 2 |
| Cetyl alcohol | | 1 | | 3 | | |
| Acrylates/$C_{10-30}$ Alkyl Acrylate Crosspolymer | | 0.2 | | | 0.1 | |
| Carbomer | | 0.2 | 0.3 | 0.2 | | |
| Xanthan Gum | 0.4 | | 0.2 | 0.2 | 0.3 | 0.4 |
| $C_{12-15}$ alkyl benzoate | 5 | 3 | | | 5 | |
| $C_{12-13}$ alkyl tartrate | | 2 | | | | |
| Butylene glycol dicaprylate/dicaprate | 5 | | | | 3 | 3 |
| Dicaprylyl Ether | | | | 2 | | |
| Octyldodecanol | 2 | | | | | |
| Dicapryl caprate | | 2 | | | 2 | 2 |
| Cyclomethicone | 5 | | 5 | 10 | | |
| Dimethicone | | | | 5 | | |
| Isohexadecane | | 1 | | | | |
| Butylene glycol | 5 | 8 | | | | 3 |
| Propylene gycol | | | 1 | | 5 | 3 |
| Glycerine | 3 | 5 | 7 | 10 | 3 | 3 |
| C18-C38 acid triglycerides | 0.5 | | 1 | | 1 | |
| Titanium dioxide | 5 | | | 2 | | |
| 2,2'-Methylenebis(6-(2H-benzotriazol-2-yl)-(1,1,3,3-tetramethylbutyl)phenol) | 2.5 | | | | | |
| 2,4,6-Tris(biphenyl)-1,3,5-triazine | | | 2 | | | |
| Merocyanine coupled to gelatine | 6 | | 6 | | 10 | 3 |
| Benzotriazole coupled to gelatine | | 5 | | 10 | | 3 |
| C8-C16 alkylpolyglycoside | 1 | 0.6 | | | | |
| UVASorb ® K2A | | | 2 | | | |
| Uvinul ® A Plus | 2 | | | | | 1 |
| Homosalate | | 5 | | 1 | | |
| Phenylbenzimidazole-sulfonic acid | | | 2 | | | 1 |
| Benzophenone-3 | 0.5 | | | | 1 | |
| Octyl salicylate | 5 | 5 | | 2 | | |
| Octocrylene | 2 | | | | 3 | 1 |
| Dye according to Example 1 | 0.1 | 0.2 | 0.3 | 0.4 | 0.5 | 1.0 |
| Dye according to Example 2 | 0.1 | 0.2 | 0.3 | 0.4 | 0.5 | 1.0 |
| Bis-ethylhexyloxyphenol methoxyphenyltriazine | | 3 | 2 | 1 | | |
| Parsol ® SLX | | | 3 | | | |
| Dihydroxyacetate | | | | 4 | | |
| Taurine | 0.1 | | | 0.5 | 0.2 | |
| 8-Hexadecene-1,16-dicarboxylic acid | | 0.2 | | | | |
| Vitamin E acetate | 0.2 | 0.2 | | 0.3 | 0.1 | 0.5 |
| $Na_2H_2EDTA$ | 0.1 | 0.1 | 0.2 | 0.2 | 0.2 | 0.5 |
| Perfume, preservative | q.s. | q.s. | q.s. | q.s. | q.s. | q.s. |
| Dyes, etc. | q.s. | q.s. | q.s. | q.s. | q.s. | q.s. |
| Sodium hydroxide | q.s. | q.s. | q.s. | q.s. | q.s. | q.s. |
| Water | to 100.0 | to 100.0 | to 100.0 | to 100.0 | to 100.0 | to 100.0 |

Example J

O/W Emulsions

| Emulsion | G | H | I | K | L | M |
|---|---|---|---|---|---|---|
| Ceteareth-20 | 1 | 1.5 | 1 | | | |
| Sorbitan stearate | | | 0.5 | | | |
| Glyceryl Stearate SE | | | | 1 | 1 | 1.5 |
| Emulgade F ® | | | | 2.5 | 2.5 | 3 |
| Cetearyl alcohol | | | | 1 | | |
| Stearyl alcohol | | | | | 1.5 | |
| Cetyl alcohol | | | 0.5 | | | 2 |
| Acrylates/$C_{10-30}$ Alkyl Acrylate Crosspolymer | 0.2 | 0.4 | 0.3 | 0.1 | | |
| Carbomer | | | | | 0.3 | |
| Xanthan Gum | | | | 0.4 | | 0.4 |
| $C_{12-15}$ alkyl benzoate | 5 | 3 | | | 5 | |
| 2-Phenyl benzoate | | | 2 | | | |
| Butylene glycol dicaprylate/dicaprate | 5 | | | | 3 | 2 |
| Dicaprylyl Ether | | | | | 2 | |
| Diethylhexyl naphthalate | 2 | | | | | |
| Dicapryl caprate | | | 2 | | 2 | 2 |
| Cyclomethicone | 5 | | | 5 | 10 | |
| Isohexadecane | | | | | 5 | |
| Mineral oil | | 1 | | | | |
| Propylene glycol | | | 4 | | | |
| Glycerine | 5 | 7 | 3 | 5 | 6 | 8 |
| C18-38 acid triglycerides | 0.5 | | 1 | | 1 | |
| Titanium dioxide | 5 | | 3 | 2 | | |
| Phenylbenzimidazole-sulfonic acid | 1 | | | 1 | 2 | 1 |
| Parsol ® SLX | 0.5 | 1.0 | 1.5 | 2.0 | 2.5 | 3.0 |
| Dye according to Example 1 or 2 | 0.5 | 1.0 | 3.0 | 0.5 | | |
| Dye according to Example 3 | | | 0.5 | 3.0 | 1.0 | 0.5 |
| Creatinine | 0.1 | 0.01 | 0.05 | | | |
| Creatine | 0.5 | 0.2 | 0.1 | | | |
| Liquorice extract/ licochalcone | | | | | 0.5 | |
| Vitamin E acetate | 0.2 | | | 0.5 | 0.5 | 0.5 |
| Tapioca starch | | 3 | | 0.2 | 2 | 0.5 |
| $Na_2H_2EDTA$ | 0.1 | | 0.2 | | | 0.5 |
| Perfume, preservative | q.s. | q.s. | q.s. | q.s. | q.s. | q.s. |
| Pigment dyes | q.s. | q.s. | q.s. | q.s. | q.s. | q.s. |
| Sodium hydroxide | q.s. | q.s. | q.s. | q.s. | q.s. | q.s. |
| Water | to 100.0 | to 100.0 | to 100.0 | to 100.0 | to 100.0 | to 100.0 |

Example K

O/W Emulsions for Skin Colouring with UV Protection

| Emulsion | N | O | P | Q | R | S |
|---|---|---|---|---|---|---|
| Glyceryl stearate SE | | 2 | | 2 | | |
| Glyceryl stearate | 2 | | 2 | | | |
| PEG-40 stearate | | | 2 | | 1 | |
| PEG-10 stearate | | | | 2.5 | 1 | |
| Ceteareth-20 | | | | | | 2.6 |
| Sodium Cetyl Phosphate | | | | | 2 | |
| Glyceryl Stearate, Ceteareth-12, Ceteareth-20, Cetearyl Alcohol, Cetyl Palmitate | | | | | | 5.4 |
| Stearic acid | 3 | 2 | | | 2 | |
| Stearyl alcohol | | 2 | 2 | | | 2 |
| Stearyl alcohol | 0.5 | | 2 | | | |
| Cetyl alcohol | 3 | | | 2 | | |
| Acrylates/$C_{10-30}$ Alkyl Acrylate Crosspolymer | | | | 0.2 | | 0.4 |
| Carbomer | | | 0.3 | | 0.3 | 0.3 |
| Xanthan Gum | | | 0.3 | 0.4 | | |
| $C_{12-15}$ alkyl benzoate | 5 | | | | 5 | 3 |
| 2-Phenyl benzoate | | 5 | | | | |
| Butylene glycol dicaprylate/dicaprate | | 5 | | 4 | | 3 |

-continued

| Emulsion | N | O | P | Q | R | S |
|---|---|---|---|---|---|---|
| Dicaprylyl Ether | | 2 | | | 3 | |
| Diethylhexyl naphthalate | 3 | | | | | |
| Cyclomethicone | 2 | | 10 | 2 | | |
| Isohexadecane | | | | 2 | 3 | |
| Mineral oil | | | | | 3 | |
| Propanediol | | 3 | | 5 | | |
| Glycerine | 3 | 5 | 10 | 7 | 4 | 5 |
| Titanium dioxide | 2 | 4 | | | | |
| Zinc oxide | | | | | 2 | |
| Drometrizole Trisiloxane | | | | | 3 | |
| Ethylhexyl methoxy-cinnamate | | 6 | 5 | | | |
| Phenyl-benzimidazole-sulfonic acid | | 0.5 | 2 | | 1 | |
| Homosalate | 5 | | | 7 | | |
| Butyl meth-oxydibenzoyl-methane | | 3 | | | | |
| Bis-Ethylhexyloxy-phenol Methoxy-phenyltriazine | | | 2 | 3 | | |
| Octyl salicylate | | | | 5 | | |
| Octocrylene | | | | | 3 | |
| Dye according to Example 1 | 0.25 | 0.5 | 0.75 | 1.0 | 1.25 | 1.5 |
| Parsol ® SLX | 4 | | | | | 5 |
| PVP hexadecene copolymer | 0.5 | | 1 | | 0.8 | |
| Coenzyme Q 10 | 0.2 | 0.02 | | 0.3 | | |
| Vitamin E acetate | 0.2 | | 0.3 | | 0.8 | 0.5 |
| Na$_2$H$_2$EDTA | 0.1 | | | | | 0.5 |
| Perfume, preservative | q.s. | q.s. | q.s. | q.s. | q.s. | q.s. |
| Pigment dyes | q.s. | q.s. | q.s. | q.s. | q.s. | q.s. |
| Sodium hydroxide | q.s. | q.s. | q.s. | q.s. | q.s. | q.s. |
| Water | to 100.0 | to 100.0 | to 100.0 | to 100.0 | to 100.0 | to 100.0 |

Example L

Aqueous and Aqueous/Alcoholic Formulations

| | A | E | C | D | E | F |
|---|---|---|---|---|---|---|
| Ethanol | 50 | 5 | 2 | 40 | 15 | |
| Hydroxyethylcellulose | 0.5 | | | | | |
| Acrylates/C10-30 Alkyl Acrylate Crosspolymer | | | | 0.3 | 0.6 | |
| Cocoatnidopropyl-betaine | | | 0.3 | | | |
| UVASorb ® K2A | | | | | 2 | |
| Uvinul ® APlus | 5 | | | | | |
| Butyl methoxydibenzoyl-methane | 0.5 | | | 3 | | |
| Disodium phenyl-dibenzimidazoletetra-sulfonate | | 2 | 1 | | | |
| Phenylbenzimidazole-sulfonic acid | | 5 | 3 | | 2 | 4 |
| Dye according to Example 1 | 0.1 | 0.25 | 0.5 | 1 | 2 | 3 |
| Dye according to Example 2 | 3 | 2 | 1 | 0.5 | 0.25 | 0.1 |
| Dye according to Example 3 | 0.1 | 0.25 | 0.5 | 1 | 2 | 3 |
| Dye according to Example 4 | 3 | 2 | 1 | 0.5 | 0.25 | 0.1 |
| Dye according to Example 5 | 0.5 | 0.5 | 0.5 | 0.5 | 0.5 | 0.5 |
| C$_{12-15}$ alkyl benzoate | | | | | 3 | |
| C18-36 triglyceride fatty acid | | | | | 1 | |
| Butylene glycol dicaprylate/dicaprate | 2 | | | | | |
| C12-13 alkyl tartrate | | | | | 5 | |
| Cyclomethicone | 4 | | | 2 | | |
| Insect repellent ® 3535 | | | | | 5 | |
| Dimethicone | | | | | 3 | |
| PVP hexadecene copolymer | | 0.5 | | 1 | | 0.5 |
| Ethylhexyloxy-glycerine | | 0.5 | | | | |
| Glycerine | 5 | 7 | 3 | 8 | | S |
| Butylene glycol | | | 5 | | 5 | |
| Metylpropanediol | | | | 4 | | |
| Vitamin E acetate | | 0.3 | 0.2 | 0.5 | | |
| Panthenol | 0.5 | | 0.2 | | | 0.3 |
| Creatinine | | | 0.01 | | 0.02 | |
| Creatine | | | 0.1 | | 0.2 | |
| PEG-40 hydrogenated castor oil | | 0.5 | 0.3 | | | 0.5 |
| Trisodium EDTA | 0.3 | 0.2 | 0.2 | 0.2 | 0.2 | 0.5 |
| Preservative | q.s. | q.s. | q.s. | q.s. | q.s. | q.s. |
| Sodium hydroxide | q.s. | q.s. | q.s. | q.s. | q.s. | q.s. |
| Perfume, dyes | q.s. | q.s. | q.s. | q.s. | q.s. | q.s. |
| Water | to 100 | to 100 | to 100 | to 100 | to 100 | to 100 |

Example M

Cosmetic Foams

| Emulsion | A | B | C |
|---|---|---|---|
| Stearic acid | 2 | 2 | |
| Palmitic acid | | | 1.5 |
| Cetyl alcohol | 2.5 | 2 | |
| Stearyl alcohol | | | 3 |
| PEG-100 stearate | | | 3.5 |
| PEG-40 stearate | | 2 | |
| PEG-20 stearate | 3 | | |
| Sorbitan stearate | | 0.8 | |
| C$_{12-15}$ alkyl benzoate | 5 | | |
| C$_{12-13}$ alkyl tartrate | | | 7 |
| Butylene glycol dicaprylate/dicaprate | | 6 | |
| Dicaprylyl Ether | | | 2 |
| Cyclomethicone | | 2 | 3 |
| Butylene glycol | 1 | | |
| Isohexadecane | 2 | | |
| Methylpropanediol | | | |
| Propylene glycol | | | 5 |
| Glycerine | 5 | 7 | |
| UVASorb ® K2A | | | 2 |
| Uvinul ® A Plus | 2 | 3 | |
| Parsol SLX ® | | 3 | |
| Dye according to Example 1 | 1.0 | | |
| Dye according to Example 2 | | 2.0 | |
| Dye according to Example 3 | | | 1.5 |
| Dye according to Example 4 | | | 1.5 |
| Dye according to Example 5 | | 1.0 | |
| Octocrylene | 2 | | |
| Bis-Ethylhexyloxyphenol Methoxyphenyltriazine | | 3 | |
| 2,2'-Methylenebis(6-(2H-benzotriazol-2-yl)-4-(1,1,3,3-tetramethylbutyl)phenol) | | | 8 |

Example N

Cosmetic Foams

| Emulsion | A | B | C |
|---|---|---|---|
| 2,4,6-Tris-(biphenyl)-1,3 5-triazine | 5 | | 4 |
| C8-C16 alkylpolyglycosides | 1 | | |
| Vitamin E acetate | 0.6 | 0.5 | 0.2 |
| Creatine/creatinine | | | 0.5 |
| BHT | | | 0.1 |
| Na$_2$H$_2$EDTA | 0.50 | | |
| Perfume, preservative | q.s. | q.s. | q.s. |
| Dyes, etc. | q.s. | q.s. | q.s. |
| Sodium hydroxide | q.s. | | q.s. |
| Potassium hydroxide | | q.s. | |
| Water | to 100.0 | to 100.0 | to 100.0 |

Example N

Cosmetic Foams

| Emulsion | D | E | F | G |
|---|---|---|---|---|
| Stearic acid | 2 | | | |
| Palmitic acid | | | 3 | 3 |
| Cetyl alcohol | 2 | 2 | | |
| Cetylstearyl alcohol | | | 2 | 2 |
| Stearyl alcohol | | | | |
| PEG-100 stearate | | 4 | | |
| PEG-40 stearate | 2 | | | |
| PEG-20 stearate | | | 3 | 3 |
| Sorbitan stearate | 0.8 | | | |
| Tridecyl Trimellitate | | 5 | | |
| C$_{12-15}$ alkyl benzoate | | | 3 | 3 |
| Butylene glycol dicaprylate/dicaprate | 8 | | | |
| Octyldodecanol | | 2 | | |
| Cocoglyceride | | | | 2 |
| Dicaprylyl Ether | | | 2 | 2 |
| Cyclomethicone | | | | |
| Dimethicone | 1 | | 2 | 2 |
| Isohexadecane | | 3 | | |
| Methylpropanediol | | 4 | | |
| Propylene glycol | | | | |
| Glycerine | 5 | | 6 | 6 |
| NeoHeliopan ® AP | | 2 | | |
| Phenylbenzimidazole-sulfonic acid | 1 | | | 1 |
| Dye according to Example 1 | 0.5 | 0.5 | 0.5 | 0.5 |
| Ethylhexyl methoxy-cinnamate | 5 | | 4 | 4 |
| Ethylhexyltriazone | | 2 | | 1 |
| Eusolex T-AVO ® | 2 | | | |
| Diethylhexylbutamido-triazone | 1 | | | |
| Butylmethoxydibenzoyl-methane | 2.5 | | 2 | 2 |
| Bis-Ethylhexyloxyphenol Methoxyphenyltriazine | 2 | | | |
| Vitamin E acetate | 0.2 | | 0.3 | 0.3 |
| Na$_2$H$_2$EDTA | | | | |
| Perfume, preservative | | | | |
| Dyes, etc. | | | | |
| Sodium hydroxide | | q.s. | q.s. | |
| Triethanolamine | q.s. | | | q.s. |
| Water | to 100.0 | to 100.0 | to 100.0 | to 100.0 |

The invention claimed is:

1. A compound of the formula I

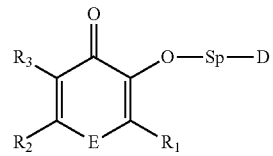

where

E denotes NR$_4$ or O,

Sp denotes a bond, alk, —C(O)— or —(CO)-alk,

D denotes a colour chromophore,

R$_1$, R$_2$ or R$_3$ each, independently of one another, denote —H, -A, —OA-, —(CH$_2$)$_p$—OH, —C(O)OA, COOH or COOX, p denotes an integer from 1 to 4, X is the counterion to the [COO$^-$] group, R$_4$ denotes A, alk denotes a linear or branched or cyclic alkylene group having 1 to 18 C atoms and A denotes a linear or branched alkyl group having 1 to 20 C atoms and/or salts, tautomers, stereoisomers and/or solvates thereof, including mixtures thereof in all ratios, wherein substituent D is a substituent of the formula II, III, IV, V, VI, VII, VIII, IX, X, XI or XII,

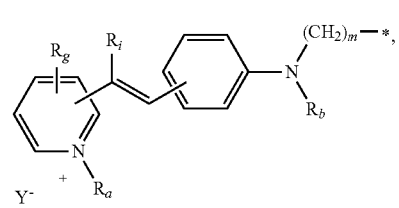

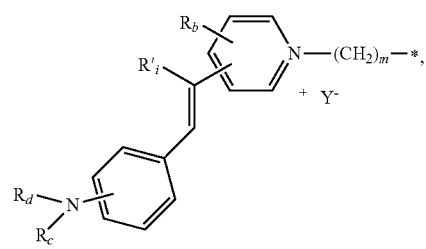

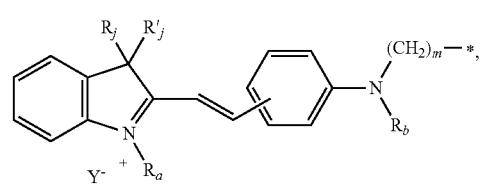

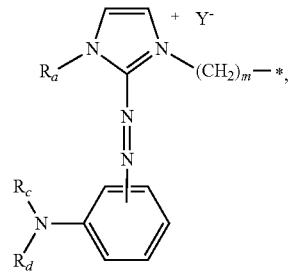

-continued

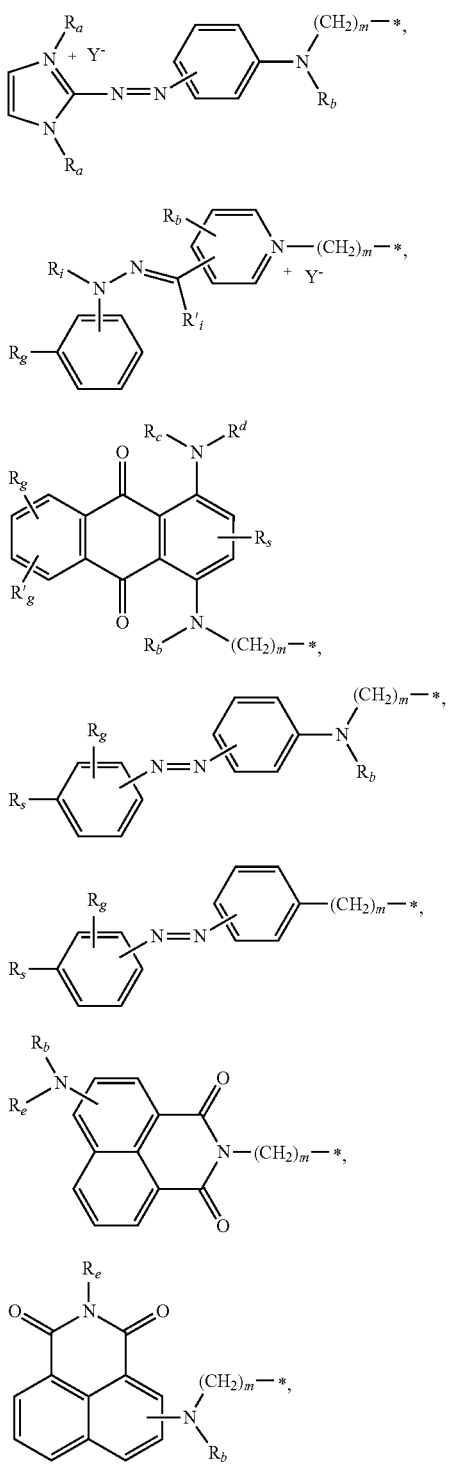

where
$R_a$, $R_j$ and $R'_j$ each, independently of one another, denote A,
$R_b$ denotes H or A,
$R_g$ and $R'_g$ each, independently of one another, denote H, Hal, $NA_2$, CN, COOH, OH, $CF_3$, OA, OC(O)A, C(O)OA, NHC(O)A, $NHSO_2A$, $SO_2NA_2$,
$R_s$ denotes H, A, $NA_2$, OA or $SO_3Y$,
$R_i$ and $R'_i$ each, independently of one another, denote H or A,
$R_c$ and $R_d$ each, independently of one another, denote H or A, where A may be substituted by at least one OH group,
$R_e$ denotes an alkyl group having 1 to 6 C atoms which is substituted by at least one group $NA_2$ or $NA_3Y$,
Y is an anion of an organic or inorganic acid or a cation,
A denotes a linear or branched alkyl group having 1 to 20 C atoms,
Hal denotes F, Cl, Br or I and
m denotes 0, 1, 2, 3, 4 or 5.

2. A compound according to claim 1, characterised in that $R_1$ denotes A.

3. A compound according to claim 1, characterised in that $R_2$ and $R_3$ denote H.

4. A compound according to claim 1, characterised in that Sp denotes —C(O)—.

5. Process for the preparation of compounds of the formula I according to claim 1, characterised in that a compound of the formula XIII

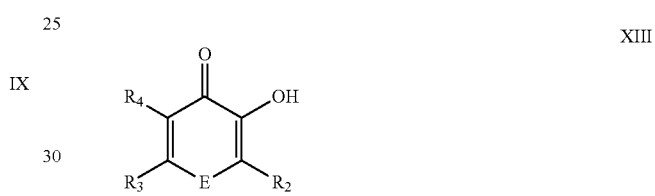

in which $R_2$, $R_3$, $R_4$ and E have a meaning indicated in claim 1, is reacted with a compound of the formula XIV D-Sp-M  XIV, in which D and Sp have a meaning indicated in claim 1, and M denotes alkali-metal or alkaline-earth metal cation, halogen, OH or H or a compound of the formula XIII, in which $R_2$, $R_3$, $R_4$ and E have a meaning indicated in claim 1, is reacted with an active ester of the compound of the formula XIV, derived from the free acid of the formula XIV, in which M denotes OH and Sp denotes —C(O)— and D has a meaning indicated in claim 1.

6. Preparation comprising at least one compound of the formula I according to claim 1.

7. Preparation according to claim 6, characterised in that it comprises a cosmetic, dermatological or pharmacologically tolerated vehicle.

8. Process for the manufacture of a preparation according to claim 7, characterised in that at least one compound of the formula I is mixed with a vehicle and optionally with further active substances or assistants.

9. A method which comprises using a compound of the formula I, according to claim 1 as a protein-adhesive dye.

10. Method for coloring a protein-containing matrix, in which the matrix is colored directly in one coloring step by the action of a dispersion and/or solution and/or emulsion of at least one compound of the formula I according to claim 1 on the matrix.

* * * * *